(12) United States Patent
Marcelpoil et al.

(10) Patent No.: US 7,899,623 B2
(45) Date of Patent: Mar. 1, 2011

(54) METHODS AND COMPUTER PROGRAM PRODUCTS FOR ANALYSIS AND OPTIMIZATION OF MARKER CANDIDATES FOR CANCER PROGNOSIS

(75) Inventors: Raphael Marcelpoil, Grenoble (FR); Clark Merrill Whitehead, Apex, NC (US); Timothy J. Fischer, Raleigh, NC (US)

(73) Assignee: TriPath Imaging, Inc., Burlington, NC (US)

( * ) Notice: Subject to any disclaimer, the term of this patent is extended or adjusted under 35 U.S.C. 154(b) by 1112 days.

(21) Appl. No.: 11/233,243

(22) Filed: Sep. 22, 2005

(65) Prior Publication Data

US 2006/0078926 A1  Apr. 13, 2006

Related U.S. Application Data

(60) Provisional application No. 60/611,965, filed on Sep. 22, 2004, provisional application No. 60/612,073, filed on Sep. 22, 2004.

(51) Int. Cl.
*G01N 33/48* (2006.01)
*G01N 21/25* (2006.01)
*G06K 9/00* (2006.01)

(52) U.S. Cl. ............. 702/19; 356/39; 356/406; 382/128; 382/129; 382/133; 702/20

(58) Field of Classification Search ........................ None
See application file for complete search history.

(56) References Cited

U.S. PATENT DOCUMENTS

2003/0091221 A1   5/2003   Marcelpoil et al.
2003/0138140 A1   7/2003   Marcelpoil et al.

FOREIGN PATENT DOCUMENTS

WO    WO-97/12247 A1    4/1997

OTHER PUBLICATIONS

Lehr et al., The Journal of Histochemistry & Cytochemistry, vol. 47, No. 1, pp. 119-125, 1999.*
Beliën et al., "Counting Mitoses by Image Processing in Feulgen Stained Breast Cancer Sections: the Influence of Resolution," *Cytometry*, 1997, vol. 28, pp. 135-140.
Bol et al., "Proliferation Markers and DNA Content Analysis in Urinary Bladder TaT1 Urothelial Cell Carcinomas: Identification of Subgroups with Low and High Stage Progression Risks," *J. Clin. Pathol.*, 2003, vol. 56, pp. 447-452.

* cited by examiner

*Primary Examiner* — Shubo (Joe) Zhou
(74) *Attorney, Agent, or Firm* — Alston & Bird LLP

(57) ABSTRACT

Methods and computer program products for evaluating and optimizing one or more markers for use in establishing a prognosis for a patient suffering from a disease are provided. More particularly, the methods include steps for systematically evaluating a number of features that may be extracted from an image of a body sample, such as a histological slide, that has been exposed to one or more biomarkers so as to establish a prognostic decision rule based on one or more of the extracted features such that the decision rule yields a prognosis that is optimally predictive of actual patient outcome. Thus, the methods and computer program products provided yield optimally predictive prognoses to assist clinicians in developing strategies for effective patient care management.

31 Claims, 5 Drawing Sheets

METHODS AND COMPUTER PROGRAM PRODUCTS FOR ANALYSIS AND OPTIMIZATION OF MARKER CANDIDATES FOR CANCER PROGNOSIS

CROSS-REFERENCE TO RELATED APPLICATIONS

This application claims the benefit of U.S. Provisional Application No. 60/611,965, filed Sep. 22, 2004, and U.S. Provisional Application No. 60/612,073, filed Sep. 22, 2004, both of which are incorporated herein by reference in their entirety.

FIELD OF THE INVENTION

The present invention relates to methods for choosing, analyzing, and optimizing biomarkers that may be candidates for use in establishing the prognosis of a patient afflicted with cancer.

BACKGROUND OF THE INVENTION

Gene amplification, gene deletion, and gene mutation are known to have a prominent role in abnormal cellular behaviors through abnormal protein expression. The range of cellular behaviors of concern includes behaviors as diverse as, for example, proliferation or differentiation regulation. Therefore, effective detection and quantification in gene amplification, deletion and mutation, mRNA quantification, or protein expression analyses is necessary in order to facilitate useful research, diagnostic and prognostic tools in complex diseases such as, for instance, various forms of cancer.

There are numerous laboratory techniques directed to detection and quantification in gene amplification, deletion and mutation, mRNA quantification, or protein expression analyses. For example, such techniques include Western, Northern and Southern blots, polymerase chain reaction ("PCR"), enzyme-linked immunoseparation assay ("ELISA"), and comparative genomic hybridization ("CGH") techniques. However, microscopy is routinely utilized because it is an informative technique, allowing rapid investigations at the cellular and sub-cellular levels while capable of being expeditiously implemented at a relatively low cost.

When microscopy is the chosen laboratory technique, the biological samples must first undergo specific detection and revelation preparations. Once the samples are prepared, a human expert typically analyzes the samples with a microscope alone in a qualitative study, or with a microscope coupled to a camera and a computer in a quantitative and generally standardized study. In some instances, the microscope may be configured for fully automatic analysis, wherein the microscope is automated with a motorized stage and focus, motorized objective changers, automatic light intensity controls and the like.

The preparation of the samples for detection may involve different types of preparation techniques that are suited to microscopic imaging analysis, such as, for example, hybridization-based and immunolabeling-based preparation techniques. Such detection techniques may be coupled with appropriate revelation techniques, such as, for example, fluorescence-based and visible color reaction-based techniques.

In Situ Hybridization ("ISH") and Fluorescent In Situ Hybridization ("FISH") are detection and revelation techniques used, for example, for detection and quantification in genetic information amplification and mutation analyses. Both ISH and FISH can be applied to histological or cytological samples. These techniques use specific complementary probes for recognizing corresponding precise sequences. Depending on the technique used, the specific probe may include a colorimetric (cISH) marker or a fluorescent (FISH) marker, wherein the samples are then analyzed using a transmission microscope or a fluorescence microscope, respectively. The use of a colorimetric marker or a fluorescent marker depends on the goal of the user, each type of marker having corresponding advantages over the other in particular instances.

Imaging and microscopy techniques have been developed to optimize and standardize the reading of colorimetric markers or stains that may be used to detect and/or quantify gene amplification, gene deletion, gene mutations, and abnormal protein expression that may be visible upon analyzing a tissue section slide treated with an appropriate marker chosen to highlight the abnormal cellular activity that may aid in the diagnosis and/or determination of prognosis for a disease such as cancer.

Such methods are useful for obtaining a quantitative measurement of a target molecular species within a given tissue sample, however, if additional molecular species are highlighted within the same tissue sample by additional biomarkers, they may be not immediately perceptible and there exists a need to identify and quantify such features in order to more systematically analyze a tissue sample so as to allow a clinician to provide a more accurate prognosis for patient suffering from a complex disease such as cancer. For instance, in many types of cancer, a small percentage of patients who are diagnosed at an early-stage still eventually have a poor ten-year outcome such as disease recurrence, metastasis, or death within this ten-year period. The majority of cancer patients diagnosed at an early stage, however, has a good 10-year prognosis and is unlikely to need, or benefit from, additional aggressive adjuvant therapy (e.g., chemotherapy). For example, the current clinical consensus is that at least some early-stage, node-negative breast cancer patients should receive adjuvant chemotherapy, but presently there are no FDA-approved assays to risk stratify patients for more aggressive treatment. Since the majority of these early-stage breast cancer patients enjoy long-term survival following surgery and/or radiation therapy without further treatment, it is likely inappropriate to recommend aggressive adjuvant therapy for all of these patients, particularly in light of the significant side effects associated with cancer chemotherapeutics. Compositions and methods that permit the differentiation of these populations of early-stage breast cancer patients at the time of initial diagnosis into good and bad prognosis groups would assist clinicians in selecting appropriate courses of treatment. Thus, methods for evaluating the prognosis of breast cancer patients, particularly early-stage breast cancer patients, are needed.

Although current prognostic criteria and quantitative video-microscopy analyses of markers provide some guidance in predicting patient outcome and selecting appropriate course of treatment, a significant need exists for a systematic method that utilizes clinical video-microscopy data to provide an optimally specific and sensitive cancer prognosis, particularly in early-stage patients. In addition there exists a need for a method for identifying and evaluating candidate markers and features thereof identified via video-microscopy, to aid in the evaluation of cancer prognosis.

SUMMARY OF THE INVENTION

A method and computer program product for analyzing and/or evaluating at least one marker adapted to determine a prognosis of a cancer patient is provided. The method for analyzing at least one marker to determine the prognosis of a cancer patient comprises the steps of: exposing a body sample (taken from the cancer patient) to the at least one marker; extracting at least one quantifiable feature from an image taken of at least one slide using an image processing system, wherein the at least one slide is prepared from the body sample; and applying a decision rule to the at least one quantifiable feature, so as to determine the prognosis of the cancer patient based on a relationship between the at least one quantifiable feature and the decision rule. In some embodiments of the method for analyzing the at least one marker, the applying step further comprises applying a threshold to the at least one quantifiable feature so as to determine the prognosis of the cancer patient based on a relationship between the at least one quantifiable feature and the threshold. In yet another embodiment of the method for analyzing the at least one marker the applying step further comprises applying an affectation rule for the threshold, the affectation rule being capable of establishing a either a good prognosis or a bad prognosis corresponding to a value of the at least one quantifiable feature in relation to the threshold.

The method for evaluating at least one marker includes the step of exposing a plurality of body samples to the at least one marker, the plurality of body samples being taken from a corresponding plurality of patients, wherein each patient has a known outcome. The method further includes the step of extracting at least one quantifiable feature from an image taken of each of a plurality of slides using an image processing system. The plurality of slides may be prepared from the plurality of body samples corresponding to each patient. Furthermore, the method includes the steps of applying a plurality of candidate decision rules to the at least one quantifiable feature of each of the plurality of slides so as to provide a corresponding candidate prognosis for each of the plurality of slides; and selecting an optimal decision rule, wherein the optimal decision rule is selected from the candidate decision rules, for the at least one quantifiable feature. The optimal decision rule provides that the candidate prognosis for each of the plurality of slides optimally corresponds to the known outcome for each of the plurality of patients. For instance, the optimal decision rule may be chosen by determining the specificity and sensitivity for each of the candidate decisions rules and choosing the decision rule having a specificity and sensitivity that is nearest the optimal specificity and sensitivity couple of (1,1).

Some embodiments of the method and computer program product of the present invention further comprise the step of evaluating the statistical independence of the at least one marker so as to ensure that the at least one marker is capable of providing a prognosis that is substantially statistically independent of at least one complementary marker. More particularly, the evaluating step above may, in some embodiments, further comprise the steps of: first, comparing a frequency distribution of observed outcomes to a frequency distribution of theoretical prognoses for a first plurality of body samples exposed to the at least one marker and to the at least one complementary marker, the first plurality of body samples corresponding to patients having a known good outcome; second, comparing a frequency distribution of observed outcomes to a frequency distribution of theoretical prognoses for a second plurality of body samples exposed to the at least one marker and to the at least one complementary marker, the second plurality of body samples corresponding to patients having a known bad outcome; and finally, assessing the independence of the at least one marker with respect to the at least one complementary marker (using, in some cases, a chi-square analysis).

According to some embodiments, the applying step of the method for evaluating may further include applying a plurality of candidate thresholds to each quantifiable feature so as to generate a plurality of candidate prognoses corresponding to each of the plurality of candidate thresholds for each of the plurality of body samples. Furthermore, the selecting step may further include selecting an optimal threshold value from the plurality of candidate thresholds such that candidate prognosis for each of the plurality of slides optimally corresponds to the known outcome for each of the plurality of patients. Such an optimal threshold may provide, for instance, a tool for use by a computerized image processing system to categorize a given value determined for a particular quantifiable feature of a marker after it has been applied to a body sample (such as a histological slide). Once categorized as either above or below the optimal threshold, the given value may then be translated into a result of the applied decision rule that may, in turn be used to establish a prognosis for the patient from whom the body sample was taken.

In other embodiments, the applying step may further comprise determining an affectation rule for each of the plurality of candidate thresholds, the affectation rule being capable of establishing either a good prognosis or a bad prognosis corresponding to a value of the at least one quantifiable feature in relation to each of the plurality of candidate thresholds.

According to various embodiments of the present invention, the method may include exposing the plurality of body samples to at least one marker wherein the marker may be chosen from the following: colorimetric biomarkers, SLPI, PSMB9, NDRG-1, Muc-1, phospho-p27, src, E2F1, p21ras, p53, and combinations thereof. Additionally, in some embodiments, the method may include extracting at least one quantifiable feature from an image taken of each of a plurality of slides wherein the quantifiable feature is detectable and quantifiable by an image processing system. Such quantifiable features may include: transmittance; optical density; cell morphology; percentage of cell types; and combinations thereof.

The method steps summarized above may also be embodied in one or more appropriate computer program products executable on a computer device (such as a computer device in communication with a microscopy system and/or image analysis system suitable for capturing an image of a stained histological slide) and capable of accomplishing the various functions associated with the method embodiments described above. For instance, according to one embodiment a computer program product is provided that may be capable of controlling an image processing system to determine a prognosis of a cancer patient, wherein the computer program comprises: (1) an executable portion for extracting a feature from an image taken of each of the plurality of slides using an image processing system, the plurality of slides being prepared from a plurality of body samples taken from a plurality of patients, wherein each patient has a known outcome, the plurality of body samples having been exposed to at least one marker; (2) an executable portion for applying a plurality of candidate decision rules to the feature of each of the plurality of slides so as to provide a candidate prognosis for each possible combination of the candidate decision rules and the feature; and (3) an executable portion for selecting an optimal decision rule corresponding to an optimal prognosis, the optimal decision rule being selected from the candidate decision rules, for the feature, the optimal decision rule providing that the optimal prognosis for each of the plurality of slides optimally corresponds to the known outcome for each of the patients.

Thus, the optimal decision rule may provide, based on the known outcomes of the plurality of patients, a prognosis that is based on the comprehensive analysis of at least one marker, having at least one quantifiable feature such that the prognosis provides a minimum number of false positive prognoses and false negative prognoses when compared to the known outcomes of the plurality of patients. Thus, once chosen, the optimal decision rule may be utilized to optimize the analysis of one or more colorimetric markers, having one or more features that are quantifiable (by, for instance, analysis in an image processing system) so as to provide patient prognoses that may more accurately predict good or bad outcomes. Thus, the method and computer program product of the present invention may allow clinicians to better utilize a given marker (or suite of markers) to predict the incidence of bad outcomes even in patients exhibiting only early-stage manifestations of a particular disease.

BRIEF DESCRIPTION OF THE DRAWINGS

Figure 1:
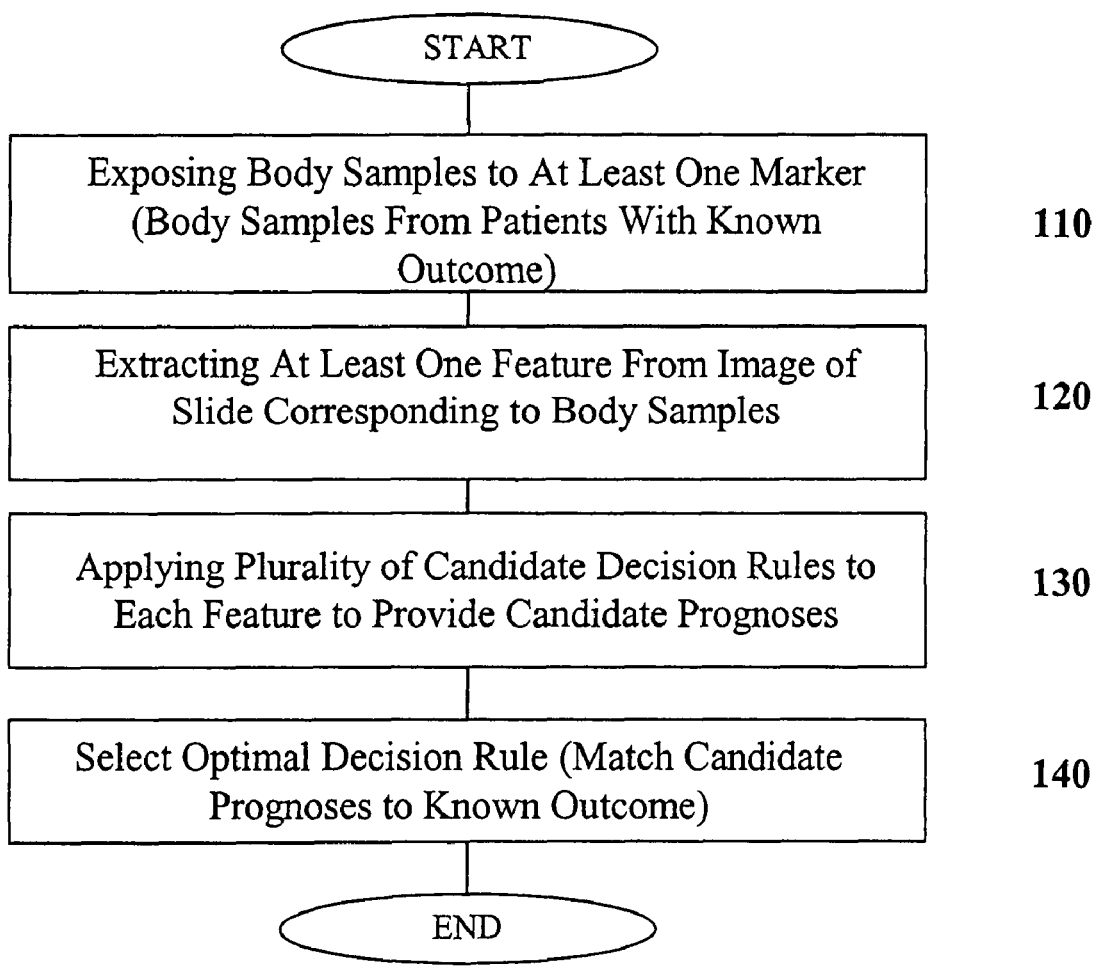
Figure 2:
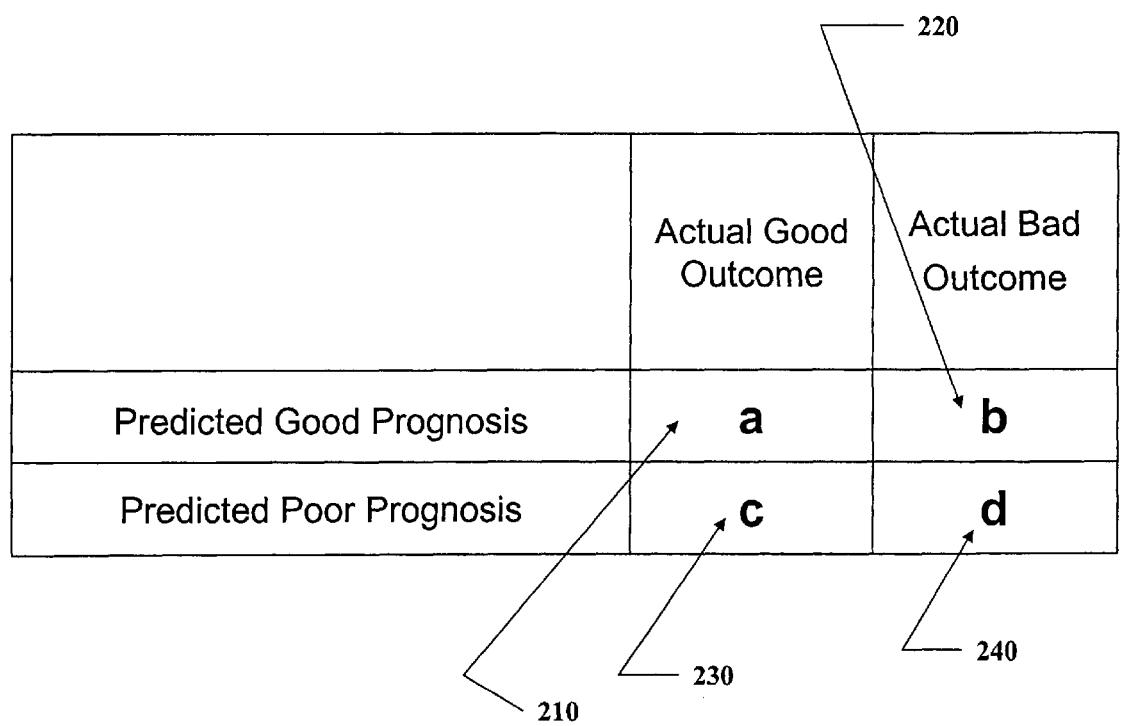
Figure 3:
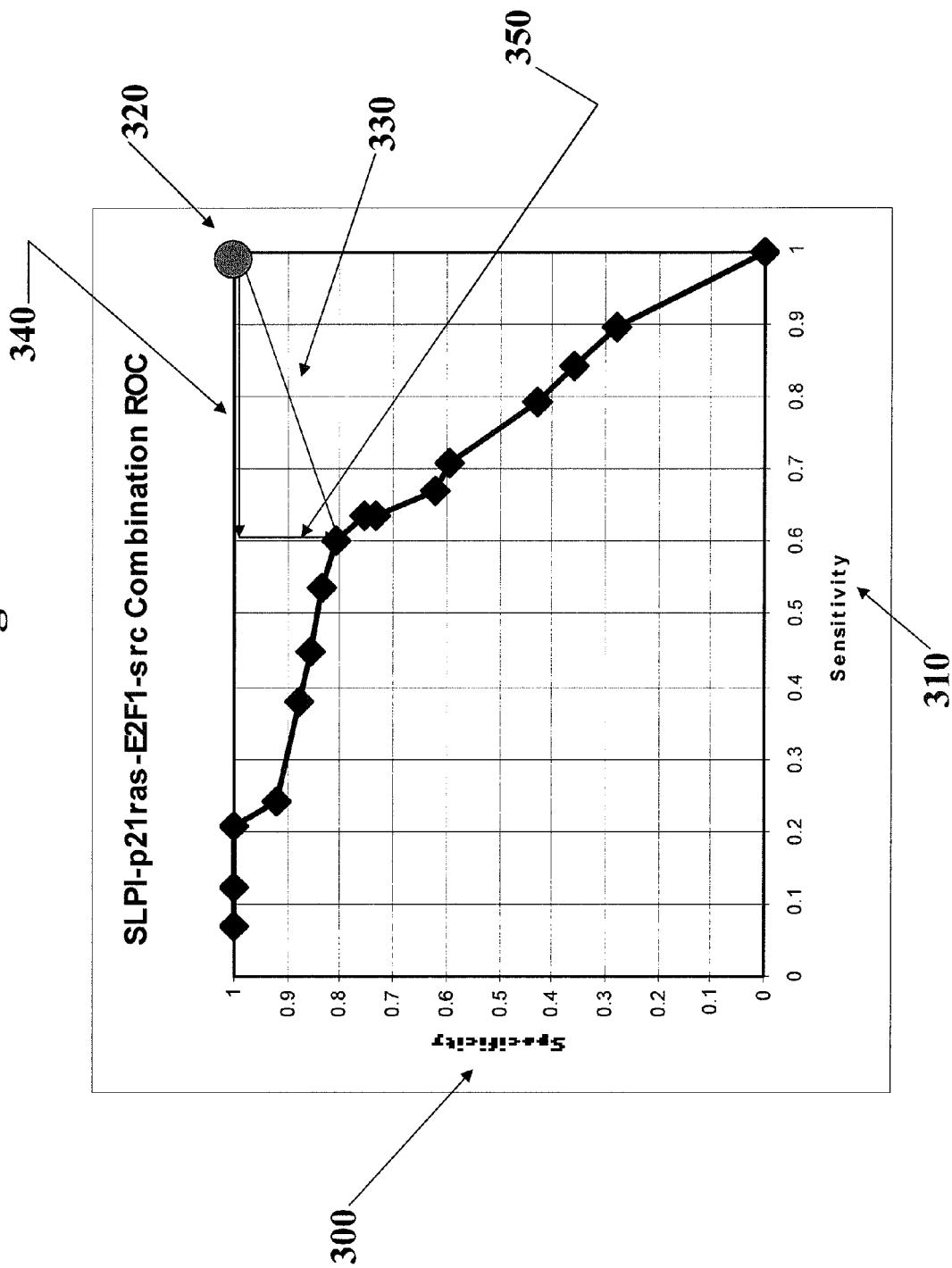
Figure 4:
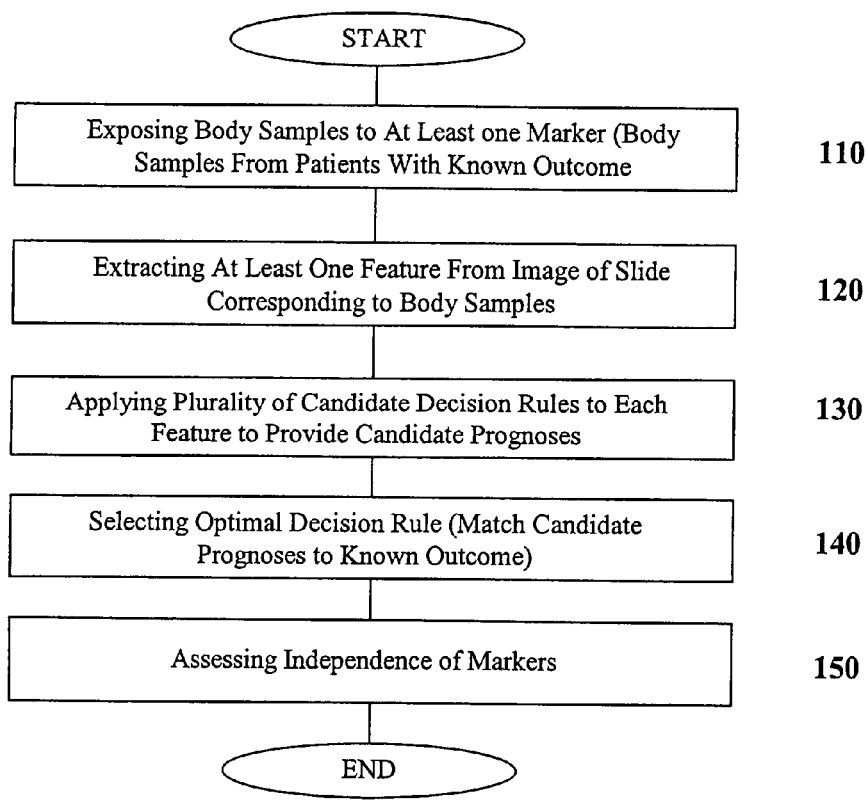
Figure 5:
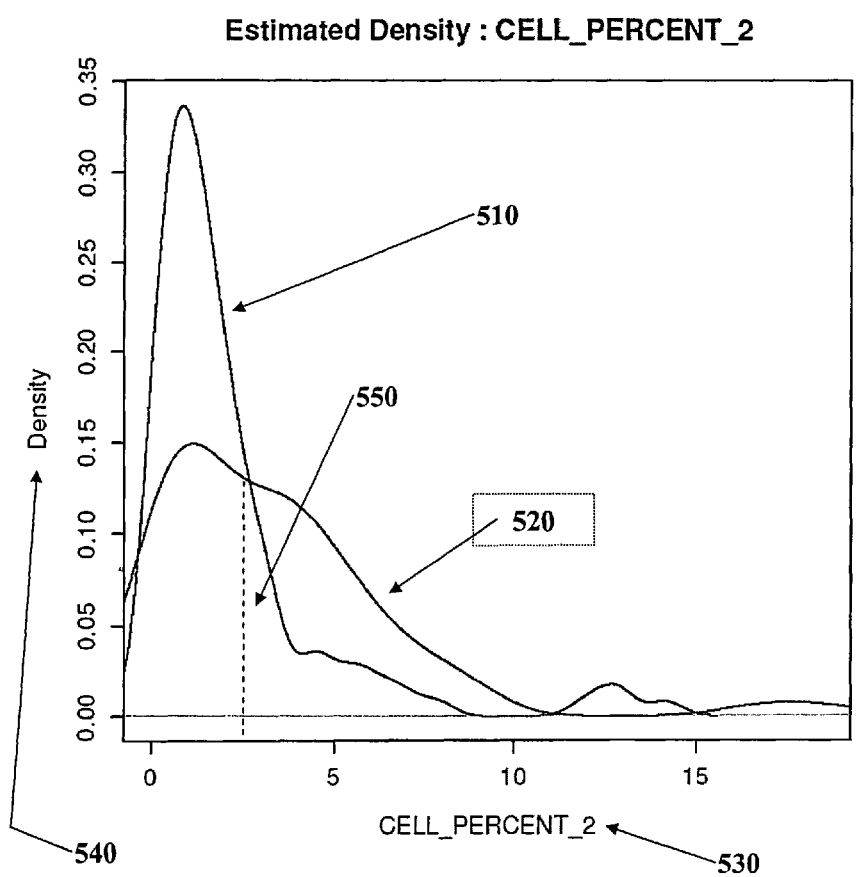

Having thus described the invention in general terms, reference will now be made to the accompanying figures, which are not necessarily drawn to scale, and wherein:

FIG. 1 shows a block diagram of the method and computer program product for evaluating at least one marker according to one embodiment of the present invention;

FIG. 2 shows a graphical representation of the four possible quadrants within which a candidate prognosis may lie when compared to a corresponding actual outcome—the depicted quadrants may be used to generate a sensitivity and specificity couple for a candidate prognosis;

FIG. 3 shows an example of an ROC curve of plotted sensitivity and specificity couples that may be used to select an optimal combination of marker features and/or thresholds so as to maximize both the sensitivity and specificity of the prognosis established by a marker or combination of markers according to one embodiment of the present invention;

FIG. 4 shows a block diagram of the method and computer program product for evaluating at least one marker and assessing the independence of the at least one marker with respect to at least one complementary marker according to one embodiment of the present invention; and FIG. 5 shows a visual representation of the determination of an optimal threshold for a given feature in a single marker analysis by plotting the distributions of good and bad outcomes on a scale of candidate thresholds.

DETAILED DESCRIPTION OF THE INVENTION

The present invention provides methods for evaluating and optimizing marker candidates for use in establishing the prognosis of a cancer patient. While the markers (and particular features thereof) described below are particularly useful for establishing a prognosis for a breast cancer patient, and more particularly an early-stage breast cancer patient, the methods disclosed herein may be utilized to evaluate and optimize marker candidates for use in establishing the prognosis of a patient suffering from any disease that may be linked to (via, for instance, clinical data) the overexpression of a particular protein or other target molecule that is amenable to staining via, for instance, a colorimetric biomarker (marker). Thus, one skilled in the art will appreciate that the methods disclosed herein may be applicable to the analysis and optimization of markers for use in establishing the prognosis of patients having other forms of cancer or other diseases linked to the expression of proteins or target molecules that may be marked and subsequently analyzed via microscopy.

The methods disclosed herein also find use in evaluating markers that may be useful in predicting the response of a breast cancer patient to a selected treatment. By "predicting the response of a breast cancer patient to a selected treatment" is intended assessing the likelihood that a patient will experience a positive or negative outcome with a particular treatment. As used herein, "indicative of a positive treatment outcome" refers to an increased likelihood that the patient will experience beneficial results from the selected treatment (e.g., complete or partial remission, reduced tumor size, etc.). By "indicative of a negative treatment outcome" is intended an increased likelihood that the patient will not benefit from the selected treatment with respect to the progression of the underlying breast cancer. In some aspects of the invention, the selected treatment is chemotherapy.

The methods disclosed herein may also find use in evaluating and/or optimizing markers useful in identifying or diagnosing cancer, particularly breast cancer. "Diagnosing breast cancer" is intended to include, for example, diagnosing or detecting the presence of breast cancer, monitoring the progression of the disease, and identifying or detecting cells or samples that are indicative of breast cancer. The terms diagnosing, detecting, and identifying cancer are used interchangeably herein. In particular embodiments, the methods of the invention may facilitate the detection of early-stage breast cancer by optimizing the markers and/or marker combinations that are most effective in diagnosing breast cancer or other diseases that may be characterized and/or diagnosed by the detection of a given marker as it is either overexpressed or presents an expression loss in a body sample (such as a stained histological slide or cytological slide).

The methods described herein relate to the application of a plurality of threshold values to a selected feature of a given marker (biomarker or colorimetric biomarker) whose overexpression may be indicative of either a good outcome or bad outcome for a given patient. One skilled in the art will appreciate that the methods of the present invention may be applied to markers showing expression loss such as, for example, melastatin which shows expression loss in cases of melanoma. Furthermore, the methods of the present invention permit the differentiation of patients that are likely to experience disease recurrence (i.e., poor prognosis) from those who are more likely to remain cancer-free (i.e., good prognosis) based on the systematic analysis of quantifiable features (and the plurality of threshold values applied thereto) that may be highlighted by colorimetric analysis of tissue samples (such as prepared histological slides) that have been exposed to one or more biomarkers. More particularly, the methods of the present invention involve a systematic process of evaluating features of a given tissue sample that have been exposed to a marker (such as a colorimetric biomarker) and choosing optimal threshold values for each feature such that the marker may be analyzed in terms of the features and corresponding optimal thresholds so that the marker/threshold combinations provide prognoses that are most accurate when compared to known actual patient outcomes. Thus, the methods of the present invention may further be used to select optimal combinations of markers, features thereof, and threshold values for each particular feature so as to provide more accurate prognoses for early stage cancer patients.

The biomarkers evaluated by the invention include genes and proteins. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides.

A "biomarker" is any gene or protein whose level of expression in a tissue or cell is altered compared to that of a normal or healthy cell or tissue. The biomarkers, according to one embodiment of the present invention, are genes and proteins whose overexpression correlates with cancer prognosis, and particularly, in the examples presented herein, breast cancer prognosis. In some cases, selective overexpression of a biomarker or combination of biomarkers of interest in a patient sample is indicative of a poor cancer prognosis. By "indicative of a poor prognosis" is intended that overexpression of the particular biomarker is associated with an increased likelihood of relapse or recurrence of the underlying cancer or tumor, metastasis, or death within less than five years. Biomarkers that are indicative of a poor prognosis may be referred to herein as "bad outcome biomarkers." In other aspects of the invention, selective overexpression of a biomarker or combination of biomarkers of interest is indicative of a good prognosis. As used herein, "indicative of a good prognosis" refers to an increased likelihood that the patient will remain cancer-free for at least five years. Such biomarkers may be referred to as "good outcome biomarkers."

The biomarkers that may be evaluated by the methods of the present invention include any gene or protein whose overexpression correlates with a cancer prognosis, as described above. Biomarkers include genes and proteins that are indicative of a poor cancer prognosis (i.e., bad outcome biomarkers) as well as those that are indicative of a good prognosis (i.e., good outcome biomarkers). Biomarkers of particular interest include genes and proteins that are involved in regulation of cell growth and proliferation, cell cycle control, DNA replication and transcription, apoptosis, signal transduction, angiogenesis/lymphogenesis, or metastasis. In some embodiments, the biomarkers regulate protease systems involved in tissue remodeling, extracellular matrix degradation, and adjacent tissue invasion. Although any biomarker whose overexpression is indicative of cancer prognosis may be analyzed and/or utilized in the method of the present invention, in particular embodiments evaluating breast cancer prognoses, biomarkers are selected from the group consisting of SLPI, p21ras, MUC-1, DARPP-32, phospho-p27, src, MGC 14832, myc, TGFβ-3, SERHL, E2F1, PDGFRα, NDRG-1, MCM2, PSMB9, MCM6, and p53. More preferably, the biomarkers of interest in establishing breast cancer prognoses comprise SLPI, PSMB9, NDRG-1, Muc-1, phospho-p27, src, E2F1, p21ras, or p53. In one aspect of the invention, as illustrated in the experimental example included herein, the methods for evaluating breast cancer prognosis comprise detecting the overexpression of E2F1 and at least one other biomarker selected from the group consisting of SLPI, src, phoshp-p27, p21ras, and PSMB9.

The term "feature" as discussed herein refers to a perceptible and/or quantifiable variation produced in a body sample by exposure to a given marker and/or biomarker. Features may include variations in transmittance or optical density values produced by the staining characteristics of a colorimetric marker (including the markers discussed above) that may be detected, for instance, using microscopy techniques and image processing systems. Such microscopy techniques and/or image processing systems are used to provide an image of the biological sample after it has been stained to visually indicate the presence of a particular biomarker of interest (and thus indicate the presence of a corresponding particular protein and/or target molecule of interest). Some of these methods and associated systems, such as those disclosed in U.S. patent application Ser. No. 09/957,446 to Marcelpoil et al. (the '446 application) and U.S. patent application Ser. No. 10/057,729 to Marcelpoil et al. (the '729 application), incorporated herein by reference, disclose the use of an image processing system, method, and associated computer program product to determine the relative amounts of each molecular species present in a given image based on the presence of representative color dye markers as indicated by those color dye markers' optical density or transmittance value, respectively, as determined by an imaging system and associated software. These techniques may further provide quantitative determinations of the relative amounts of each target molecule or protein whose overexpression may be revealed by a colorimetric biomarker applied to a tissue sample slide. For instance, the expression of a feature of a given marker may be revealed using a digital image of a marked tissue sample slide wherein the marker is separated from background stain and/or other markers using chromogen separation from its component red, green, and blue (RGB) color parts such that the relative contribution of the marker (relative to background stain and/or staining from other markers) may be determined within a cell or a region of interest (ROI) within a body sample taken from a patient.

According to the various embodiments of the present invention, various features (both quantifiable and non-quantifiable) may be extracted from an image taken from a marked tissue sample (such as a prepared histological slide stained with a colorimetric biomarker) using an image processing system capable of capturing regions of interest (ROI), various fields of view (FOV) or images of entire histological slides and determining morphological boundaries defined therein such as the various regions of the cell including the nucleus, cytoplasm, and cell membrane. This image processing step for determining morphological boundaries within a slide and/or body sample is known as segmentation. Regions of interest (ROI) may, according to various embodiments, span an entire slide, portions of a slide, discrete selected portions of a slide, and/or an entire FOV. Accurate segmentation of the morphological boundaries (via microscopy and/or image analysis) is required for the determination of many features as various different biomarker types exhibit different sub-cellular location within the cells of a given body sample. For instance, some biomarkers reveal overexpression of a target molecule only within the nucleus of a cell. Other markers may reveal overexpression of a target molecule within the cytoplasm or within the cell membrane of a cell. For instance, Table 1 shows some of markers used in establishing a prognosis and/or diagnosis for breast cancer are listed along with their respective areas of sub-cellular localization.

As described in the attached Appendix of Example Features, certain cell descriptor features such as CELL, CYTO, MEMB, and NUCL (referring to the cell, cytoplasm, cell membrane, and cell nucleus, respectively) serve as location identifiers within the cells of a body sample wherein the features exhibited by a particular marker may be detected and/or quantified using, for instance, chromagen separation of a dye or stain.

Also shown in the attached appendix are a number of other exemplary features of various biomarkers that may be extracted, examined, and or quantified by the methods of the present invention in order to optimize the prognostic value of a given biomarker or combination of biomarkers. The features are categorized generally as follows: shape descriptor features; texture and/or histogram descriptor features (which refer mainly to statistical determinations as to the amount and variation of target molecule overexpression that may be highlighted by a particular biomarker); spectral descriptor features (such as transmittance or optical density of the various colorimetric biomarkers and/or counterstains that may be used to reveal overexpression of the target molecules); hierarchy descriptor features (which are used to compute quantifiable features relative to hierarchical objects captured by an imaging system); and cellular descriptor features (including CELL, CYTO, MEMB, and NUCL (as described above and detailed in the Appendix of Example Features). The list of features described generally above and in more detail in the appendix attached hereto is not meant to be exhaustive and is meant to serve only as an example. The method of the present invention may utilize a variety of different quantifiable features (and various combinations thereof) in order to optimize the prognostic value of a given marker or combination of markers. According to the computer program product embodiments of the present invention, the features described herein may be detected in an automated manner by, for instance, a controller (such as a computer device) configured to control an image processing system having the capability of marking regions of interest (ROI), segmenting the various compartments and components of a cell or tissue sample, and/or deconstructing a stain or dye into component RGB parts so as to determine transmittance, luminance, optical density and/or other spectral features.

In some embodiments of the present invention, the features above and others may be combined to create summary features that incorporate several types of underlying features in order to create a quantifiable feature that may have utility for the purposes of providing a diagnosis and/or prognosis of a given patient. In order to construct such a summary feature, other more specific features may be quantified and examined in order to create the summary feature which may, in some cases, have more significance to a clinician seeking to obtain prognostic and/or diagnostic value from the features highlighted by a biomarker and/or collection of biomarkers. For instance, in the Experimental Example described herein, the features utilized include numerical percentages of various grades of cancer cells that are deemed present in a given collection of cells that may be highlighted in a specific region of interest (ROI) identified in a body sample (such as an histological slide). One skilled in the art will appreciate that a pathologist may "grade" a cell that has been stained with a marker as it is viewed, for instance, via microscopy, by ascertaining the degree of marker that is present in the region of interest (ROI) (such as an area of a histological slide that appears to be stained darker than the surrounding regions). While visual grading by a pathologist is helpful for ascertaining the relative level of marker present in a cell, such grading is fairly subjective and may vary according to various clinicians and in various contexts. Thus, in building a summary feature in the present invention, suspected cancer cells may be more objectively graded as, for instance, either 0 (indicating a complete lack of marker present in the targeted cell compartment), 1 (indicating some small amount of marker present in the targeted cell compartment), 2 (indicating a medium level of marker present in the targeted cell compartment), or 3 (indicating a high level of marker present in the targeted cell compartment). Such grading may be accomplished in an automated manner using a video-microscopy system and/or image processing system such as those disclosed in the '446 application and the '729 application. As summarized below in Table 2, according to one example of the present invention, the features denoted by NUCL, CYTO, MEMB, DYE2, OD, and MEAN may be combined to produce optical transmittance values having a range of values that may be partitioned to determine the level of the given colorimetric biomarker (or in some instances, a colorimetric component thereof) (denoted by "DYE2," for instance) in a given cell. The same dye may be used to render the given biomarker a colorimetric biomarker (such as, for instance, a commonly used dye stain such as DAB or others well-known to one skilled in the art) however, the various different markers evaluated by the present invention may reveal the existence of target molecules in various cell compartments (such as the nucleus, cell membrane, and/or cytoplasm). The example threshold values (corresponding to transmittance values), in this case shown in Table 2 may thus dispatch each of the viewed cells into a one of the following categories: 0, 1, 2, or 3. An evaluation of category 0 corresponding to the expected number of non-stained cells (i.e. cells found not to exhibit overexpression of the target molecule when exposed to the marker) may be performed using an image processing system and/or microscopy. The approximate number of 0 (non-stained) cells may further be computed using the average tumor cell area (for instance, 1100 pixels as estimated from the feature called CELL_AREA (See Appendix of Example Features)) obtained, in this particular embodiment, from calculations of 1, 2 and 3 cells area (using the determinations listed below):

$$N_1 = N_{NegRef} \quad (1)$$

$$N_2 = N_{Test} \quad (2)$$

$$N_3 = N_{PosRef} \quad (3)$$

$$N_{Total} = \max\left(N_1 + N_2 + N_3, \frac{FOCUS\_AREA}{1100}\right) \quad (4)$$

$$N_0 = \max(0, N_{Total} - N_1 - N_2 - N_3) \quad (5)$$

In other embodiments the number of cells may be computed using methods other than determining the cell areas (such as by counting nuclei within a FOV that are stained with a nucleus localized marker). Once the number of 0, 1, 2, and 3 cell types ($N_0$, $N_1$, $N_2$ and $N_3$, respectively) is determined (using, for instance, the various threshold values given in Table 2), the percentage of 0, 1, 2 and 3 cells may be computed. Table 3 presents the names of these new summary features using the prefix CELL_PERCENT along with a numerical identifier showing the types of cells reflected in the given percentage. These example summary features may be computed as simple percentage. For example, CELL_PERCENT_0 may be computed as follows:

$$CELL\_PERCENT\_0 = \frac{N_0}{N_{Total}} \times 100. \quad (6)$$

Although the CELL_PERCENT summary features described above are used in the experimental example described herein, any number of possible quantifiable features may be evaluated as part of the embodiments of the methods and computer program products of the present invention. For example, one or more of the colorimetric features disclosed in the Appendix of Example Features (associated with, for instance, the analysis of a stained histological slide using an image analysis system) may be combined to form another type of summary feature or individual features described in the Appendix may be used and analyzed independently.

The various features and summary features described above may be applicable in the analysis of one or more markers that may be used to stain a body sample (or a slide prepared therefrom, such as, for example, a histological slide) in order to establish (or aid in the establishment of) a prognosis for a cancer patient (such as an early-stage breast cancer patient). According to the embodiments of the present invention, different combinations of markers and features thereof, may be evaluated using the embodiments of the present invention to establish an optimal combination of features, feature thresholds (such as a given CELL_PERCENT of Type-2 cancer cells in a given region of interest (ROI)), and marker types such that the sensitivity and specificity of a given marker or marker combination may be optimized. In addition, other types of patient-based features may be combined with the features disclosed herein such as (but not limited to): patient age; patient medical history; and other factors indicating possible prognosis and/or diagnosis for cancer patients. For example, lymph node involvement, tumor size, histologic grade, estrogen and progesterone receptor levels, Her 2/neu status, tumor ploidy, and family history may all be prognostic and/or diagnostic factors to aid in the establishment of a prognosis for an early-stage breast cancer patient.

Using the methods and computer program products of the present invention, features, thresholds, and marker combinations may be efficiently and systematically analyzed and evaluated to determine an optimal specificity and sensitivity in establishing a prognosis for any given cancer patient. In the methods and computer program products of the present invention, the endpoint for assessing specificity and sensitivity is comparison of the prognosis (for example, the outcome predicted using a particular candidate marker and/or corresponding candidate feature or features) with the actual clinical outcome (i.e., whether the patient remained cancer-free or suffered a recurrence within five years). As shown in FIG. 2, the candidate prognoses produced by a number of candidate feature/threshold combinations may be plotted in a four-quadrant matrix as shown based on the known outcomes of the body samples used in the methods of the present invention to determine the numbers of true positive 210, true negative 240, false positive 220, and false negative 230 prognoses produced by a given marker/feature (and/or decision rule) combination as described in more detail below. After computing relative numbers of true positive 210, true negative 240, false positive 220, and false negative 230 prognoses, a characteristic sensitivity and specificity couple may be computed to assess the effectiveness of the marker/feature/decision rule combination as a prognostic tool (as described in more detail below)

As used herein, "specificity" refers to the level at which a method of the invention can accurately identify true negatives. In a clinical study, specificity is calculated by dividing the number of true negatives by the sum of true negatives and false positives (as determined by plotting candidate prognoses in the quadrants of FIG. 2). By "sensitivity" is intended the level at which a method of the invention can accurately identify samples that are true positives. Sensitivity is calculated in a clinical study by dividing the number of true positives by the sum of true positives and false negatives (also as determined by plotting candidate prognoses in the quadrants of FIG. 2). In some embodiments, the sensitivity of a given combination of markers, features, and thresholds uncovered by the disclosed methods is at least about 40%, 45%, 50%, 55%, 60%, 65%, 70%, 75%, 80%, 85%, 90%, 91%, 92%, 93%, 94%, 95%, 96%, 97%, 98%, 99% or more. Furthermore, the specificity attainable by the present evaluation methods is preferably at least about 40%, 45%, 50%, 55%, 60%, 65%, 70%, 75%, 80%, 85%, 90%, 91%, 92%, 93%, 94%, 95%, 96%, 97%, 98%, 99% or more.

As used herein, the definitions of "true" and "false" positives and negatives will be dependent upon whether the marker or combination of markers under consideration is good outcome or bad outcome markers. That is, in the case of good outcome markers (i.e., those indicative of a good prognosis), "true positive" refers to those samples exhibiting overexpression of the biomarker of interest, as determined by the methods of the invention (e.g., positive staining by immunohistochemistry), that have a confirmed good actual clinical outcome. In contrast, "false positives" display overexpression of the good outcome biomarker(s) but have a confirmed bad actual clinical outcome. "True negatives" and "false negatives" with respect to good outcome markers do not display marker overexpression (e.g., do not stain positive in immunohistochemistry methods) and have confirmed bad and good actual clinical outcomes, respectively.

Similarly, in the case of bad outcome markers, "true positives" refers to those samples exhibiting overexpression of the marker or combination markers of interest that have a confirmed bad actual clinical outcome. In summary, "true positive" with respect to both good and bad outcome biomarkers refers to samples in which the actual clinical outcome (i.e., good or bad) is accurately predicted. "False positives" display overexpression of the bad outcome biomarker but have a confirmed good actual clinical outcome. "True negatives" and "false negatives" with respect to bad outcome biomarkers do not display biomarker overexpression and have confirmed good and bad actual clinical outcomes, respectively. The methods and computer program products of the present invention utilize a systematic comparison of prognoses produced using a number of markers, features of markers, and threshold values for given features, with actual clinical outcomes in order to determine which optimal combination of markers, features, and thresholds are most likely to provide prognoses that are the most accurate as defined by actual clinical outcomes.

FIG. 1 shows a schematic flow diagram of a method according to one embodiment of the present invention for evaluating at least one marker that may be utilized to determine a prognosis of a cancer patient. Step 110 shows an exposing step, including exposing a plurality of body samples to a marker (or in some cases, a plurality of markers). The plurality of body samples are taken, for instance, from a corresponding plurality of patients, wherein each patient has a known clinical outcome. As described in more detail above, the marker may include a variety of colorimetric biomarkers that may be used to detect a variety of target molecules (such as, for instance, proteins) that may be overexpressed in a given cell. The body samples may include biopsy tissue samples taken from patients having a disease for which the method of the present invention is being used to evaluate a marker.

Step 120 shows the next step according to one method of the present invention which includes extracting at least one quantifiable feature from an image taken of each of a plurality of slides using an image processing system, wherein the plurality of slides are prepared from the plurality of body samples corresponding to each patient having a known outcome. The slides may hold sequential sections of a biopsy core sample or other tissue sample and may be exposed to one or more of the markers that may be under evaluation as part of the methods of the present invention. The slides may include histological slides that are dyed and/or stained to facilitate the extraction of a quantifiable feature (such as a perceptible change in color, shade, luminance, transmittance (TRANS), optical density (OD), or other features as described in more detail above). For instance, the slide may be treated with a stain configured to highlight the marker (or plurality of markers) to which the body samples have been exposed. In addition, the slide may be treated with a counterstain having a color and/or staining characteristic tending to highlight the staining of the marker or markers of interest. One skilled in the art will appreciate that such colorimetric stains may include DAB (tending to stain the appearance of markers brown) and that counterstains may include hematoxylin (tending to stain the normal morphology of the cell blue). In addition, any of the stained slides may be analyzed using the chromagen separation techniques disclosed, for instance, in the '446 application and the '729 application.

As described above, the extracting step may involve extracting features from a video-microscopy image of the slide using, for instance, an image analysis system and an associated controller (such as a computer device) configured to analyze a given image (such as an entire slide, a camera field-of-view (FOV), or a selected region-of-interest (ROI)). As described in detail in the attached Appendix of Example Features, many different features relating to an image of a slide having been exposed to a given marker (or set of markers) may be extracted and analyzed. In some embodiments, a clinician such as a pathologist, may utilize an image analysis system to select a ROI (corresponding, for instance, to a region of a microscopy image stained dark with DAB so as to indicate the presence of large amounts of a given marker). Within the ROI, the image analysis system (and controller in communication therewith) may be used to isolate and extract a number of the features described in the attached appendix. For example, a number of cells within the ROI may be computed and the percentage of Type 1 cells therein may be computed as well (by applying, for instance, the dispatcher settings outlined in Table 2, after determining the optical density of light transmitted through different cell compartments (depending on marker type) contained within the ROI). In order to apply a threshold or objective decision rule ((see step 130) described in detail below), the feature is, in most cases, a quantifiable feature, such as a percentage, number of cells, area, luminance, transmittance, and/or optical density. For example, in the attached experimental example, the summary features extracted from various ROI's included the percentages of Type 1, Type 2, and Type 3 cancer cells (and combinations of these percentages) wherein the percentages were computed by combining more specific features (such as the transmittance and/or optical density of stained areas of the cells which are used to dispatch a given cell to a particular type designation (Type 1, 2, or 3, for instance)).

Step 130 of one embodiment of the method of the present invention includes applying a plurality of candidate decision rules to the extracted quantifiable feature of each of the plurality of slides so as to provide a corresponding candidate prognosis for each of the slides. The "decision rule" can be made up of several components including an affectation rule (which involves a determination of whether a quantifiable feature greater than a given threshold is indicative of a good prognosis or a bad prognosis) as well as a threshold value for a given quantifiable feature. In the analysis of a single marker having a single feature, the decision rule may be a binary decision for the particular feature. According to many embodiments of the present invention, the overall decision rule involves generating either a good or bad candidate prognosis (depending on the candidate threshold and the corresponding affectation rule). For instance, according to one embodiment, good prognoses may be denoted as zero (0), and bad prognoses may be denoted as (1). However, for each possible threshold, there are two possible choices for affectation rules (i.e. good prognoses (0) may refer to values less than the threshold value, or, alternatively, bad prognoses (1) may refer to values less than the threshold value). Thus, each affectation rule (for each possible threshold) may be evaluated for each body sample (corresponding to a patient having a known outcome) and placed in one of four quadrants corresponding to one of the following categories as shown in FIG. 2: true positives (quadrant a, 210), false positives (quadrant b, 220), false negatives (quadrant c, 230), and true negatives (quadrant d, 240). A possible prognosis may then be generated for each of the possible threshold/affectation rule combinations for each body sample (corresponding to a patient having a known outcome) such that the optimal affectation rule for each threshold may be determined by choosing for each quadrant in FIG. 2, an affectation rule, based upon the occurrence of good and bad outcomes in that quadrant.

For instance, given a threshold value (T) for a specific quantifiable feature (F) of a marker, two affectation rules are possible to determine a prognosis. The first possible rule is, if F is greater than T, the prognosis is bad (1). The second possible rule is: if F is greater than T, the prognosis is good (0). For each of these possible affectation rules, the predicted prognosis may either accurately predict the actual patient outcome (i.e. yield a true positive or true negative) or fail to predict the actual patient outcome (i.e. yield a false positive or false negative). It is possible to determine which quadrant of FIG. 2 contains most of the possible prognoses to determine which affectation rule is most appropriate for a given quantifiable feature. For example, referring to FIG. 2, the possible prognoses for the first possible rule may be plotted to determine where the results lie. In addition, the possible prognoses for the second possible rule may be plotted to determine where the results lie within the quadrants depicted in FIG. 2. After plotting both possible affectation rules in the appropriate quadrants, an optimal affectation rule may be determined by determining the ratio of predicted good versus bad outcomes normalized to the overall number of good and bad outcomes. For instance, for a given feature and threshold, most plotted points may lie in the true positive quadrant if the first possible affectation rule (if F>T, prognosis=bad (1)) is used. In this case, the following candidate decision rule may be generated: patients exhibiting the quantifiable feature above the threshold are considered to have a bad prognosis (positive for the disease). In another example, most plotted points may lie in the false negative quadrant if the first possible rule if F<T, prognosis=good (0) is used. In this case, the candidate decision rule may read as: patients exhibiting the quantified feature above the threshold are considered to have a good prognosis (negative for the disease). One skilled in the art will appreciate that other statistical methods may also be utilized to find efficient decision rules. For instance, linear discrimination, quadratic discrimination, generalized linear models, logistic regressions, penalized discrimination, flexible discrimination, mixture discrimination, and/or other statistical methods may be utilized to find such decision rules as part of step 130 of the present invention.

As shown in FIG. 1, step 140 includes selecting an optimal decision rule, selected from the candidate decision rules, for the at least one quantifiable feature. The optimal decision rule is chosen so as to provide that the candidate prognosis for each of the plurality of slides optimally corresponds to the known outcome for each of the plurality of patients. For example, the decision rule is chosen from the plurality of candidate decision rules so as to provide an optimally predictive prognosis tool that produces the minimum number of false negatives and false positives when compared to the clinical outcomes of the patients from whom the body samples have been taken (see Step 110). As described above, the candidate decision rules have both a threshold component and an affectation rule component. By systematically evaluating a plurality of candidate thresholds (and affectation rules) an optimal threshold value may be chosen such that the optimal prognosis resulting therefrom for each of the plurality of slides may correspond most closely to the known outcome for each of the plurality of patients (from which the plurality of slides are produced). Additionally, the efficiency of a given decision rule may be tested using specificity and sensitivity as shown below in equations 7 and 8.

According to some embodiments of the present invention, selecting an optimal decision rule further comprises determining a plurality of specificity and sensitivity couples corresponding to each of the plurality of candidate decision rules. In such embodiments, the specificity and sensitivity for each candidate decision rule (and for each of the plurality of candidate thresholds and corresponding affectation rules) may be computed by comparing the candidate prognosis from each candidate decision rule to the actual known outcome for each patient from which the body samples were taken. In performing this comparison each the relative numbers of true positives (quadrant a), false positives (quadrant b), false negatives (quadrant c), and true negatives (quadrant d) may be determined using a quadrant system such as that depicted in FIG. 2. Using the relative numbers for each quadrant, sensitivity and specificity couples (sens, spec) may be computed for each candidate decision rule and each of the plurality of candidate thresholds using the following formulas:

$$\text{Sensitivity} = \frac{a}{(a+c)} \quad (7)$$

$$\text{Specificity} = \frac{d}{(b+d)} \quad (8)$$

Thus, as described generally above, sensitivity refers to the probability of a bad outcome patient being evaluated as being positive in regard to the marker (i.e. to be considered as a true positive). Similarly, specificity refers to the probability of a good outcome patient being evaluated as being negative in regards to the marker (i.e. to be considered a true negative).

Each of the sensitivity and specificity couples may then be plotted on two-dimensional sensitivity and specificity chart as shown in FIG. 3 wherein each point refers to the specificity and sensitivity value calculated for each of the plurality of candidate decision rules (and for each of the plurality of candidate thresholds). The chart shown in FIG. 3 is also known as receiver operating characteristic (ROC) curve shows a plot of sensitivity values 310 and corresponding specificity values 300 for a set of candidate decision rules that have been compared to a set of data corresponding to actual clinical outcomes. An ideal prognostic test would have an ideal sensitivity and specificity couple 320 plotted at point 1,1 which indicates that all the prognostic results consist of either true positives or true negatives (see quadrants a 210 and d 240 in FIG. 2). For each plotted sensitivity and specificity couple on the ROC curve, the Euclidian distance may be computed between the plotted couple and the ideal couple 320 at (1,1) using the specificity difference 350 and the sensitivity difference 340 between the plotted and ideal couples. After plotting the ROC curve as shown in FIG. 3, the specificity and sensitivity couple having the minimum Euclidian distance 320 to the ideal couple 320 may be identified such that the optimal decision rule (and corresponding optimal threshold and/or affectation rule) may be selected in order to target a specific sensitivity and specificity couple of the marker and feature combination under evaluation. Furthermore, in some embodiments, the optimal decision rule may be selected in order to maximize both the sensitivity and specificity (i.e. approach the ideal (1,1) sensitivity and specificity couple) of the marker and feature combination under evaluation.

As shown in FIG. 4, some methods of the present invention may further comprise an additional step, shown schematically in block 150, which includes evaluating the statistical independence of at least one marker so as to ensure that the marker is capable of providing a prognosis that is substantially statistically independent of at least one complementary marker. Thus, this embodiment may ensure that for a given pair of markers applied to a body sample, the prognoses generated therefrom are substantially statistically independent such that one marker does not provide substantially repetitive information with regard to the complementary marker. This may ensure, for instance, that a complementary marker is not used in conjunction with a first marker when the two are not substantially statistically independent. The dependence of the two markers may indicate that they are duplicative and that the addition of a second marker adds no additional value to the prognostic power of a given pair of markers. In order to optimize the prognostic power of a given panel of markers it is also desirable to reduce the amount of signal "noise" by minimizing the use of markers that provide duplicative prognostic information when compared to another marker in the panel.

The evaluation of the statistical independence of the two markers may involve, for instance, in some embodiments, the following additional steps: (1) comparing a frequency distribution of observed outcomes to a frequency distribution of theoretical prognoses for a first set of body samples exposed to a first marker and to a complementary marker, wherein the first set of body samples correspond to patients having a known good outcome; (2) comparing a frequency distribution of observed outcomes to a frequency distribution of theoretical prognoses for a second set of body samples exposed to the first marker and to the complementary marker, wherein the second set of body samples correspond to patients having a known bad outcome; and (3) assessing the independence of the at least one marker with respect to the at least one complementary marker using a chi square ($X^2$) analysis.

For example, a $X^2$ analysis may be performed in order to assess marker independence when considering 2 markers at a time and taking the outcome of the patients (corresponding to the body samples) into account. Table 7 details how the $X^2$ value was obtained for both good and bad outcome patient sub-populations for a particular marker pair. According to one example, the $X^2$ value was computed to be 7.81 with a probability of error (p) of 0.05. Thus, the following results may follow: (1) if $X^2_{Good} < 7.81$, then $H_0$Good cannot be rejected; (2) If $X^2_{Bad} < 7.81$, $H_0$Bad cannot be rejected; and thus (3) If ($X^2_{Good} < 7.81$ and $X^2_{Bad} < 7.81$) $H_0$ cannot be rejected, and the markers can be considered independent.

The methods disclosed herein may also be embodied in one or more appropriate computer program products executable on a computer device (such as a computer device in communication with a microscopy system and/or image analysis system suitable for capturing an image of a stained histological slide or cytological slide) and capable of accomplishing the various functions associated with the methods and associated systems described herein. More particularly, steps 120, 130, 140, and 150 of the method embodiment illustrated in FIGS. 1 and 4, may be accomplished with a computer program product having one or more executable portions for accomplishing or otherwise directing the method steps to be undertaken. For example, in such computer program embodiments, the executable portions may accomplish step 120 shown in FIGS. 1 and 4 by facilitating communication between a computer device (or other controller device) and a microscopy system or image analysis system suitable for extracting one or more of the features described and detailed in the appendix of example features included herein. For example, an executable portion illustrated schematically by step 120 may be capable of extracting statistical data (or another quantifiable feature) from a digital image (obtained via an image analysis system) of a stained histological slide corresponding to the staining characteristics of a particular marker.

Additionally the executable portions of the computer program products of the present invention may also accomplish step 130 shown in FIGS. 1 and 4 via the systematic application of an exhaustive plurality of candidate decision rules to the at least one quantifiable feature extracted from each of the plurality of slides so as to generate a sequence of candidate prognoses corresponding to each of the plurality of combinations of the exhaustive plurality of decision rules (comprising, in some cases, a systematic evaluation of possible thresholds and/or affectation rules for a plurality of marker combinations and features thereof).

According to some embodiments, the executable portions of the computer program products of the present invention may also perform or facilitate step 140 shown in FIGS. 1 and 4 by calculating a specificity and sensitivity couple for each of the candidate prognoses using the known outcomes for each of the patients corresponding to the plurality of slides under investigation. Thus, the executable portion illustrate schematically in step 140 may determine a decision rule that corresponds to a targeted and/or optimal specificity and sensitivity couple.

Finally, as shown in step 150 of FIG. 4, the executable portions of the computer program products of the present invention may also direct and/or facilitate a determination of marker independence of two or more markers using chi-square analyses or other techniques as described above in relation to the method embodiments of the present invention. Such determinations may also take into account the prevalence of certain outcomes in the patient population from which the plurality of slides (and images thereof) were taken.

Thus, one skilled in the art will appreciate that the computer program product embodiments of the present invention may be utilized to systematically evaluate complex combinations of thresholds, affectation rules, and corresponding sequence-based decision rules that may result when evaluating sets of markers so as to determine a marker combination and decision rule corresponding thereto that will approach and/or reach a targeted and/or optimal specificity and sensitivity level.

One of skill in the art will appreciate that any or all steps in the methods of the invention could be implemented by personnel or, alternatively, performed in an automated fashion. Thus, the steps of body sample preparation (see step 110, for instance), sample staining (see step 110, for instance), and detection of biomarker expression (see step 120, for instance) may be automated. Moreover, in some embodiments, the immunohistochemical methods of the invention are used in conjunction with computerized imaging equipment and/or software to facilitate the identification of positive-staining cells by a pathologist. The methods disclosed herein can also be combined with other prognostic methods or analyses (e.g., tumor size, lymph node status, expression levels of other biomarkers (including, for instance, Her2/neu, Ki67, estrogen receptor (ER), progesterone receptor (PR) and p53). In this manner optimization and evaluation of the biomarkers using the methods described herein may facilitate the detection of overexpression of the various biomarkers evaluated by the invention so as to permit a more accurate determination of the prognosis of a patient suffering from a disease that may be linked to the overexpression of one or more of the various biomarkers.

In addition, many modifications and other embodiments of the invention will come to mind to one skilled in the art to which this invention pertains having the benefit of the teachings presented in the foregoing descriptions and the associated drawings, appendices and examples. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The following experimental example describes the use of the embodiments of the present invention in evaluating an example panel of 4 candidate biomarkers and quantifiable summary features thereof that may be used in establishing prognoses for breast cancer patients. It is offered by way of illustration and not by way of limitation.

Experimental Example

Evaluation of a Panel of Biomarkers (SLPI, p21ras, E2F1 and src) for Establishing Breast Cancer Prognoses Introduction:

According to the experimental example included herein, the embodiments of the present invention may be used to evaluate a combination of biomarkers whose overexpression may be useful for establishing diagnoses and prognoses for patients having various types of breast cancer. In the case of the appended experimental example, and, in other embodiments of the present invention, a panel of markers may be evaluated to determine an optimal sequence-based decision rule. By "breast cancer" is intended, for example, those conditions classified by biopsy as malignant pathology. The clinical delineation of breast cancer diagnoses is well-known in the medical arts. One of skill in the art will appreciate that breast cancer refers to any malignancy of the breast tissue, including, for example, carcinomas and sarcomas. In particular embodiments, the breast cancer is ductal carcinoma in situ (DCIS), lobular carcinoma in situ (LCIS), or mucinous carcinoma. Breast cancer also refers to infiltrating ductal (IDC) or infiltrating lobular carcinoma (ILC). In most embodiments of the invention, the subject of interest is a human patient suspected of or actually diagnosed with breast cancer.

The American Joint Committee on Cancer (AJCC) has developed a standardized system for breast cancer staging using a "TNM" classification scheme. Patients are assessed for primary tumor size (T), regional lymph node status (N), and the presence/absence of distant metastasis (M) and then classified into stages 0-IV based on this combination of factors. In this system, primary tumor size is categorized on a scale of 0-4 (T0=no evidence of primary tumor; T1=$\leqq$2 cm; T2=>2 cm-$\leqq$5 cm; T3=>5 cm; T4=tumor of any size with direct spread to chest wall or skin). Lymph node status is classified as N0-N3 (N0=regional lymph nodes are free of metastasis; N1=metastasis to movable, same-side axillary lymph node(s); N2=metastasis to same-side lymph node(s)

fixed to one another or to other structures; N3=metastasis to same-side lymph nodes beneath the breastbone). Metastasis is categorized by the absence (M0) or presence of distant metastases. While the evaluation of markers used to establish the prognosis of breast cancer patients at any clinical stage is encompassed by the present invention, the evaluation and optimization of markers used to establish a prognosis for a breast cancer patient in early-stage breast cancer are of particular interest. By "early-stage breast cancer" is intended stages 0 (in situ breast cancer), I (T1, N0, M0), IIA (T0-1, N1, M0 or T2, N0, M0), and IIB (T2, N1, M0 or T3, N0, M0). Early-stage breast cancer patients exhibit little or no lymph node involvement. As used herein, "lymph node involvement" or "lymph node status" refers to whether the cancer has metastasized to the lymph nodes. Breast cancer patients are classified as "lymph node-positive" or "lymph node-negative" on this basis. Methods of identifying breast cancer patients and staging the disease are well known and may include manual examination, biopsy, review of patient's and/ or family history, and imaging techniques, such as mammography, magnetic resonance imaging (MRI), and positron emission tomography (PET).

The term "prognosis" is recognized in the art and encompasses predictions about the likely course of breast cancer or breast cancer progression, particularly with respect to likelihood of disease remission, disease relapse, tumor recurrence, metastasis, and death. For the purposes of the example described herein, "good prognosis" refers to the likelihood that a patient afflicted with breast cancer, will remain disease-free (i.e., cancer-free) for at least five years, while "poor prognosis" is intended to mean the likelihood of a relapse or recurrence of the underlying cancer or tumor, metastasis, or death within less than five years. Cancer patients classified as having a "good outcome" remain free of the underlying cancer or tumor for at least five years. In contrast, "bad outcome" cancer patients experience disease relapse, tumor recurrence, metastasis, or death within five years. As used herein, the relevant time for assessing prognosis or disease-free survival time begins with the surgical removal of the tumor or suppression, mitigation, or inhibition of tumor growth.

As described herein above, a number of clinical and prognostic breast cancer factors are known in the art and are used to predict the likelihood of treatment outcome and disease recurrence. Such factors include lymph node involvement, tumor size, histologic grade, estrogen and progesterone hormone receptor status (ER/PR), Her 2/neu levels, and tumor ploidy. Using the methods of the present invention, the evaluation of a combination of markers and a feature thereof used in establishing the prognosis of an early-stage breast cancer patient can be accomplished in a systematic manner independent of or in combination with assessment of these or other clinical and prognostic factors.

The methods of the invention permit the systematic evaluation of candidate biomarkers (and features thereof) so as to provide superior assessment of breast cancer prognosis in comparison to analysis of other known prognostic indicators (e.g., lymph node involvement, tumor size, histologic grade, estrogen and progesterone receptor levels, Her 2/neu status, tumor ploidy, and family history).

Breast cancer is managed by several alternative strategies that may include, for example, surgery, radiation therapy, hormone therapy, chemotherapy, or some combination thereof. As is known in the art, treatment decisions for individual breast cancer patients can be based on the number of lymph nodes involved, estrogen and progesterone receptor status, size of the primary tumor, and stage of the disease at diagnosis. Stratification of patients into poor prognosis or good prognosis risk groups at the time of diagnosis using the methods disclosed herein may provide an additional or alternative treatment decision-making factor. The methods of the invention permit the analysis and evaluation of candidate biomarkers used to differentiate those breast cancer patients with a good prognosis from those more likely to suffer a recurrence (i.e., patients who might need or benefit from additional aggressive treatment at the time of diagnosis). The methods of the invention find particular use in choosing appropriate biomarkers, features thereof, and feature thresholds so as to maximize the prognostic value of a candidate biomarker (or panel of biomarkers) in establishing a more accurate prognosis of an early-stage breast cancer patient. As discussed above, the majority of breast cancer patients diagnosed at an early-stage of the disease enjoy long-term survival following surgery and/or radiation therapy without further adjuvant therapy. A significant percentage (approximately 20%) of these patients, however, will suffer disease recurrence or death, leading to clinical recommendations that some or all early-stage breast cancer patients should receive adjuvant therapy (e.g., chemotherapy). The methods of the present invention find use in evaluating biomarkers and features thereof that may better highlight this high-risk, poor prognosis population of early-stage breast cancer patients and thereby determining which patients would benefit from continued and/or more aggressive therapy and close monitoring following treatment.

In this experimental example, the methods of the present invention were utilized to evaluate a panel of 4 candidate biomarkers (SLPI, p21ras, E2F1 and src) and a single summary feature corresponding to each biomarker (extracted using an image-processing system). The example shows the determination of an optimal sequence-based decision rule according to one embodiment of the present invention. The features utilized in the example relate to the percentage of 1+, 2+ and 3+ cells in breast cancer tumor regions identified as regions of interest (ROI) by a pathologist. Based upon these features, sensitivity and specificity couples were maximized for the selected marker/feature combinations using optimal sequence-based decision rules (consisting of thresholds and affectation rules).

Materials and Methods:

In this experimental example, over 200 patients were analyzed in order to evaluate and optimize different marker and feature combinations for establishing breast cancer prognoses. As summarized in Table 4, this population of patients is quite heterogeneous and exhibits tumors of different stages ranging from T1N0 to T3N0. The targeted characteristic of the patients is their good outcome or bad outcome status. Good outcome patients were those still disease-free after five years; bad outcome patients were defined as patients with recurrence or death within five years. Body samples and corresponding slides taken thereof were taken from each patient so as to provide body samples having a known outcome such that specificity and sensitivity couples could be determined for each possible marker/feature/threshold combination as described above.

The body samples from the study (from the same patient population outlined in Table 4) were then exposed to the panel of 4 biomarkers (see Table 5) and corresponding slides were produced so as to subject the marked slides to the methods of the present invention. The following steps highlight the method of the present invention as it was applied in this experimental example: (1) chromagen separation was optimized for each marker that showed the best quality stain (according to the chromagen separation methods of the '446 application and the '729 application); (2) segmentation set up was customized for each marker according to its sub-cellular localization; see Table 1 (nucleus, cytoplasm or membrane). (See also the NUCL, CYTO, and MEMB features highlighted in the attached appendix of example features); and (3) features were extracted at cell, field of view (FOV) and focus level, within the defined ROI and exported to an output file (XML format).

A specific computer program product according to one embodiment of the present invention (in this example named "Multi Marker Analyzer") was then used to complete the evaluation and optimization of the marker combinations. According to one embodiment, the computer program product is configured to be capable of loading all or a portion of either tissue micro-arrays (TMA) or tissue section XML files generated using microscopy, to merge data contained in these files using XML files describing the TMA keys (in the case of a TMA analysis) or Excel files giving patient clinical status and patient evaluation (in the case of a tissue section analysis) and all the further analyzes. This merge process consists in the association of the features extracted via microscopy for each body sample (corresponding to each patient) with the information kept in the TMA key (or the Excel file) about the patient: identification number and medical status (including Good or Bad outcome) and the pathologist evaluation if it is not included in the XML formatted file.

Table 5 lists the markers evaluated in this example (SLPI, p21ras, E2F1 and src) and the corresponding CELL_PERCENT summary features extracted for each marker type (this example shows the establishment of a sequence-based decision rule for four markers wherein single-marker/single feature thresholds were analyzed to determine an optimal sequence-based decision rule). The decision rule was created using the methods of the present invention outlined in FIG. 1 wherein the predicted prognoses (for each possible sequence of markers, wherein each marker is either "on" (1) or "off" (0). In order to determine thresholds for the feature evaluated for each particular marker (see Table 5) each possible threshold amount (from 0 to 100%) was analyzed and compared to the outcomes for the various patients in the study from which the body samples for the example were taken. For example, FIG. 5 shows the distribution curves for CELL_PERCENT_2 corresponding to the E2F1 marker. The plot shows the distribution of bad outcome patients 520 and the distribution of good outcome patients 510 as a function of CELL_PERCENT_2 values. As is shown in FIG. 5, above the 2-3 percent limit, Bad Outcome patients (520) are significantly more frequent than Good Outcome patients (510). Using a threshold 550 of 2.46% would give sensitivity and specificity of 0.54 and 0.75, respectively with the use of the E2F1 marker alone as a prognostic indicator. Column 3 of Table 5 shows the resulting decision rule determined for the E2F1 marker from the data in FIG. 5 (which includes both the threshold of 2.46% and affectation rule ("on" if greater than 2.46% CELL_PERCENT_2) for E2F1).

Candidate prognoses (corresponding to each possible combination of sequences) were generated and then compared to the actual outcomes for each of the body samples being evaluated using the quadrant system in FIG. 2 in order to determine the number of true positives 210, false positives 220, false negatives 230 and true negatives 240. As described in detail above, once plotted in the appropriate quadrants, specificity and sensitivity values corresponding to each possible decision rule were computed (the results of such computations are shown in Table 6). The sequence-based decision rule determined from the data of Table 6 can be read as follows: if E2F1 is ON (i.e. 1) and not the only one marker to be ON then the patient is considered bad outcome, good outcome otherwise.

Results:

Using only one percentage feature for SLPI, p21ras, E2F1 and src with thresholds and decision rule defined in Table 5, 60% sensitivity and 80% specificity was reached on this sample set using a rather simple sequence-based decision rule: if E2F1 is ON (i.e. 1) and not the only one marker to be ON then the optimal prognosis for the patient is bad outcome. Therefore, the prognosis for the patient is good outcome otherwise.

As described above, a prognostic decision rule based on E2F1 alone would give sensitivity and specificity of 54% and 75%, respectively. However, using an interpretation-based marker combination when E2F1 is ON and either SLPI, p21ras or src is ON leads to 60% sensitivity and 80% specificity (using the sequence-based decision algorithm defined by the results of Table 6).

APPENDIX

Example Features

The following features are indicative of the types of quantifiable features that may be extracted from an image of a body sample (such as a stained histological slide or a cytological slide) using an imaging system or video-microscopy system in communication with, for instance, a controller such as a computer device. Furthermore, the following features may be extracted and/or computed using embodiments of the computer program product described herein. In some embodiments, the following features may be compounded and/or combined so as to build summary features that may be more easily utilized by a clinician to quantify a value that may correspond to a prognostic indicator for a particular disease that may be linked to the overexpression (and resulting dye staining) of a particular target molecule.

It should be understood that the following appendix of features is offered by way of illustration and not by way of limitation. One skilled in the art will appreciate that other features may be of interest and may be extracted and analyzed so as to evaluate one or markers using the methods and computer program product embodiments of the present invention.

A. Shape Descriptor Features:

1. Area

This is the number of foreground pixels in a blob (holes are not counted), which mask (binary representation) is M. When pixel to micron correspondence is available (k) it represents the physical area of the blob (M) on the slide (micrometers$^2$). If no physical correspondence of pixel to micron (k) is available AREA is the number of measured pixels (k=1).

$$\text{Area} = k^2 \times \Sigma_{p \in E} p \quad (9)$$

with $E=\{p|p \in M\}$

Range is $[0, \infty[$

2. Perimeter

This is the total length of edges in a blob (including the edges of any holes)), which mask (binary representation) is M, with an allowance made for the staircase effect that is produced when diagonal edges are digitized (inside corners are counted as $\sqrt{2}$, rather than 2.). A single pixel blob (area=1) has a perimeter of 4.0. When pixel to micron correspondence is available (k) it represents the physical perimeter of the blob (M) on the slide (micrometers). If no physical correspondence of pixel to micron is available (k=1).

$$\text{Perimeter} = k \times \Sigma_{p \in E} p \times q(n_p) \qquad (10)$$

with E={p|p∈M} and $$n_p = \left\{ \begin{matrix} & t & \\ l & p & r \\ & b & \end{matrix} \right\},$$

if p Interior and p is a Corner then $$q(n_p) = \sqrt{2}$$

else $q(n_p) = 4 - \Sigma(t,l,r,b)$
Range is $[0,\infty[$
3. Minferet

This is the smallest Feret diameter (minimum bounding diameter of a rectangular box fitting the object, found after checking a certain number of angles). When pixel to micron correspondence is available (k) it represents the physical Min Feret diameter of the blob (M) on the slide (micrometers). If no physical correspondence of pixel to micron is available (k=1).

Range is $[0,\infty[$
4. Maxferet

This is the largest Feret diameter (maximum bounding diameter of a rectangular box fitting the object, found after checking a certain number of angles). When pixel to micron correspondence is available (k) it represents the physical Max Feret diameter of the blob (M) on the slide (micrometers). If no physical correspondence of pixel to micron is available (k=1).
Range is $[0,\infty[$
5. Compactness This value is a minimum for a circle (1.0) and is derived from the perimeter (P) and area (A). The more convoluted the shape, the greater the value.

$$\text{Compactness} = \frac{P^2}{4\pi A} \qquad (11)$$

Range is $[1,\infty[$
6. Roughness

This is a measure of how rough a blob is and is equal to perimeter (P) divided by the convex perimeter ($P_c$). A smooth convex object will have the minimum roughness of 1.0

$$\text{Roughness} = \frac{P}{P_c} \qquad (12)$$

Range is [0,1]
7. Elongation

This value is equal to the true Length/Breadth. It should be used for long thin objects.
Range is $[0,\infty[$
B. Histogram Descriptor Features
1. Sum The SUM is the sum of all the individual pixel scores.

$$\text{Sum} = \sum_{i=0}^{255} i \times h(i) \qquad (13)$$

Range is $[0,\infty[$ for transmittances and for optical densities
2. Mean

The arithmetic mean is what is commonly called the average: When the word "mean" is used without a modifier, it can be assumed that it refers to the arithmetic mean. The mean is the sum of all the scores divided by the number of scores. The mean is a good measure of central tendency for roughly symmetric distributions but can be misleading in skewed distributions since it can be greatly influenced by extreme scores. Therefore, other statistics such as the median may be more informative for distributions such as reaction time or family income that are frequently very skewed.

The sum of squared deviations of scores from their mean is lower than their squared deviations from any other number.

For normal distributions, the mean is the most efficient and therefore the least subject to sample fluctuations of all measures of central tendency.

$$\text{Mean} = \frac{\sum_{i=0}^{255} i \times h(i)}{N} \text{ with } N = \sum_{i=0}^{255} h(i) \qquad (14)$$

Range is [0,1] for transmittances
Range is [0.0000,2.4065] for optical densities
3. Min The min is the smallest value of a distribution.

$$\text{Min} = i \left| \left\{ h(i) > 0, \sum_{j=0}^{j<i} h(j) = 0 \right\} \right. \qquad (15)$$

Range is [0,1] for transmittances
Range is [0.0000,2.4065] for optical densities
4. Q1

Q1 is the 25th percentile of a distribution. 25% of the scores are below Q1 and 75% are above Q1.

$$Q_1 = i \left| \left\{ \sum_{j=0}^{j<i} h(j) < \frac{N}{4}, \sum_{j=0}^{j<=i} h(j) \geq \frac{N}{4} \right\} \text{ with } N = \sum_{i=0}^{255} h(i) \right. \qquad (16)$$

Range is [0,1] for transmittances
Range is [0.0000,2.4065] for optical densities
5. Median The median is the middle of a distribution: half the scores are above the median and half are below the median. The median is less sensitive to extreme scores than the mean and this makes it a better measure than the mean for highly skewed distributions.

The sum of the absolute deviations of each number from the median is lower than is the sum of absolute deviations from any other number.

The mean, median, and mode are equal in symmetric distributions. The mean is higher than the median in positively skewed distributions and lower than the median in negatively skewed distributions $$\text{Median} = Q_2 = i \left| \left\{ \sum_{j=0}^{j<i} h(i) < \frac{N}{2}, \sum_{j=0}^{j<=i} h(i) \geq \frac{N}{2} \right\} \text{ with } N = \sum_{i=0}^{255} h(i) \right. \quad (17)$$

Range is [0,1] for transmittances
Range is [0.0000,2.4065] for optical densities

6. Q3

Q3 is the 75th percentile of a distribution. 75% of the scores are below Q3 and 25% are above Q3.

$$Q_3 = i \left| \left\{ \sum_{j=0}^{j<i} h(i) < \frac{N \times 3}{4}, \sum_{j=0}^{j<=i} h(i) \geq \frac{N \times 3}{4} \right\} \text{ with } N = \sum_{i=0}^{255} h(i) \right. \quad (18)$$

Range is [0,1] for transmittances
Range is [0.0000,2.4065] for optical densities 7. Max The max is the largest value of a distribution.

$$\text{Max} = i \left| \left\{ h(i) > 0, \sum_{j=i+1}^{255} h(i) = 0 \right\} \right. \quad (19)$$

Range is [0,1] for transmittances
Range is [0.0000,2.4065] for optical densities 8. Mode The mode is the most frequently occurring score in a distribution and is used as a measure of central tendency. The advantage of the mode as a measure of central tendency is that its meaning is obvious. Further, it is the only measure of central tendency that can be used with nominal data.

The mode is greatly subject to sample fluctuations and is therefore not recommended to be used as the only measure of central tendency. A further disadvantage of the mode is that many distributions have more than one mode. These distributions are called "multimodal."

In a normal distribution, the mean, median, and mode are identical.

$$\text{Mode} = i | \{h(i) >= h(i)_{i=0}^{255}\} \quad (20)$$

Range is [0,1] for transmittances
Range is [0.0000,2.4065] for optical densities 9. Trimean The trimean is computed by adding the 25th percentile+ twice the 50th percentile (median)+the 75th percentile and dividing by four.

The trimean is almost as resistant to extreme scores as the median and is less subject to sampling fluctuations than the arithmetic mean in skewed distributions. It is less efficient than the mean for normal distributions.

$$\text{TriMean} = \frac{Q_1 + 2Q_2 + Q_3}{4} \quad (21)$$

Range is [0,1] for transmittances
Range is [0.0000,2.4065] for optical densities 10. Trimmedmean50

A trimmed mean is calculated by discarding a certain percentage of the lowest and the highest scores and then computing the mean of the remaining scores. A mean trimmed 50% is computed by discarding the lower and higher 25% of the scores and taking the mean of the remaining scores. The median is the mean trimmed 100% and the arithmetic mean is the mean trimmed 0%.

A trimmed mean is obviously less susceptible to the effects of extreme scores than is the arithmetic mean. It is therefore less susceptible to sampling fluctuation than the mean for skewed distributions. It is less efficient than the mean for normal distributions.

$$\text{TrimmedMean}_{50} = \frac{\sum_{i=Q_1}^{i=Q_3} i \times h(i)}{\sum_{i=Q_1}^{i=Q_3} h(i)} \quad (22)$$

Range is [0,1] for transmittances
Range is [0.0000,2.4065] for optical densities 11. Range The range is the simplest measure of spread or dispersion: It is equal to the difference between the largest and the smallest values. The range can be a useful measure of spread because it is so easily understood. However, it is very sensitive to extreme scores since it is based on only two values. The range should almost never be used as the only measure of spread, but can be informative if used as a supplement to other measures of spread such as the standard deviation or semi-interquartile range.

$$\text{Range} = \text{Max} - \text{Min} \quad (23)$$

Range is [0,1] for transmittances
Range is [0.0000,2.4065] for optical densities 12. Semiinterquartilerange The semi-interquartile range is a measure of spread or dispersion. It is computed as one half the difference between the 75th percentile [often called $(Q_3)$] and the 25th percentile $(Q_1)$.

Since half the scores in a distribution lie between $Q_3$ and $Q_1$, the semi-interquartile range is ½ the distance needed to cover ½ the scores. In a symmetric distribution, an interval stretching from one semi-interquartile range below the median to one semi-interquartile above the median will contain ½ of the scores. This will not be true for a skewed distribution, however.

The semi-interquartile range is little affected by extreme scores, so it is a good measure of spread for skewed distributions. However, it is more subject to sampling fluctuation in normal distributions than is the standard deviation and therefore not often used for data that are approximately normally distributed.

$$SemiInterQuartileRange = \frac{Q_3 - Q_1}{2} \quad (24)$$

Range is [0,1] for transmittances
Range is [0.0000,2.4065] for optical densities 13. Variance The variance is a measure of how spread out a distribution is. It is computed as the average squared deviation of each number from its mean.

$$Variance = \frac{n\sum x^2 - (\sum x)^2}{n(n-1)} \quad (25)$$

Range is [0,∞[

14. STDEV

This feature estimates standard deviation based on a sample. The standard deviation is a measure of how widely values are dispersed from the average value (the mean). The standard deviation is the square root of the variance. It is the most commonly used measure of spread.

Although less sensitive to extreme scores than the range, the standard deviation is more sensitive than the semi-interquartile range. Thus, the semi-interquartile range should supplement the standard deviation when the possibility of extreme scores is present.

$$Stdev = \sqrt{\frac{n\sum x^2 - (\sum x)^2}{n(n-1)}} \quad (26)$$

Range is [0,∞[

15. Skew

This feature returns the skewness of a distribution. Skewness characterizes the degree of asymmetry of a distribution around its mean. A distribution is skewed if one of its tails is longer than the other. Positive skewness indicates a distribution with an asymmetric tail extending toward more positive values. Negative skewness indicates a distribution with an asymmetric tail extending toward more negative values.

$$Skew = \frac{n}{(n-1)(n-2)} \sum \left(\frac{x_i - \bar{x}}{S}\right)^3 \quad (27)$$

Range is ]-∞,+∞[
with S is the sample standard deviation

16. Kurtosis

This feature returns the kurtosis of a data set. Kurtosis characterizes the relative peakedness or flatness of a distribution compared with the normal distribution. Positive kurtosis indicates a relatively peaked distribution. Negative kurtosis indicates a relatively flat distribution. Kurtosis is based on the size of a distribution's tails.

$$Kurtosis = \left\{\frac{n(n+1)}{(n-1)(n-2)(n-3)} \sum \left(\frac{x_i - \bar{x}}{S}\right)^4\right\} - \frac{3(n-1)^2}{(n-2)(n-3)} \quad (28)$$

Range is ]-∞,+∞[

S is the sample standard deviation.

C. Transmittance and Optical Density Features (TRANS, OD, and Others)

1. TRANS—Transmittance

Transmittance is the ratio of the total radiant or luminous flux transmitted by a transparent object to the incident flux, usually given for normal incidence.

$$Trans = \frac{I}{I_0} \quad (29)$$

Range is [0,1]

Within images, transmittance is discretized on 8 bits leading to 256 values within [0,255] range. If underlying computation is based upon such discrete values, computed features are however expressed within [0,1] range, from 0% to 100% transmittance.

$$Trans_{255} = 255 \frac{I_{255}}{I_0 \mid 255}, [0, 255] \quad (30)$$

2. OD—Optical Density

Optical density relates to Transmittance as the negative value of its logarithm. Within images, transmittance is discretized on 8 bits leading to 256 values within [0,255] range.

$$OD = -\log_{10}(Trans) = \log_{10}\left(\frac{I_0}{I}\right) \quad (31)$$

Range is [0.0000,2.4065] due to 8 bits discretization of transmittances

Temporary OD image buffers are also discrete buffers.

$$OD_{255} = k \times \log_{10}\left(\frac{I_0 \mid 255}{I_{255}}\right) = k \times \log_{10}\left(\frac{255}{I_{255}}\right), [0, 255] \text{ with} \quad (32)$$

$$k = \frac{255}{\log_{10}(255)}, OD_{255}(Trans_{255}(0)) = OD_{255}(Trans_{255}(1))$$

If the underlying computation is based upon such discrete values, computed features are however expressed according to real OD values ranging from 0 to infinite (theoretical), cast on upper limits to 2.4065 in practice due to 8 bits constraint.

3. Luminance and Dye Features (LUMIN, DYE1, DYE2, DYE3)

The histogram features computed on Transmittance or Optical density histograms reflect either the Luminance ("LUMIN") of the RGB image or the Dye of interest calculated after solving the chromagen model for the pixel (R,G,B)

value ("DYE 1", "DYE2" or "DYE3"). The RGB chromagen separation model is described for instance in the '446 application and the '729 application.

$$\text{LUMIN}(Y) = 0.299R \; 0.587G + 0.114B \text{ Conventional floating-point equations} \quad (33)$$

$$\text{LUMIN}(Y) = [(9798 R + 19235G + 3736 B)/32768] \text{ Equations used by code} \quad (34)$$

Note: Chromagen Errors, Dye Confidence

When solved, the RGB chromagen separation model evaluates a reconstruction error, which is the Euclidean distance within the RGB space between the input RGB value of the pixel and the recomputed RGB value based upon the reconstruction of the RGB value from each dye contribution. This error can be evaluated for each and every pixel of the object of interest reported using the methods and apparatus of the RGB chromagen separation model referenced above.

Depending on the chromagen error measured for each RGB value and the noise level (NOISE) recorded within the optical system when acquiring the white reference image used to perform shading correction and image normalization, a confidence is computed for each dye based upon the probability that the transmittance evaluated for this pixel would not statistically vary more than the ability of the human eye to discriminate between different transmittances.

D. Hierarchy Descriptor Features

When computing features relative to the different hierarchical objects (such as a cell, cell membrane, nucleus, or other object) within a slide (such as a histological slide) or image of a slide, the features may be evaluated with respect to the following hierarchical reference fields: the slide (SLIDE), the focus (FOCUS), the field of view (FOV) or the cell (CELL) relative to that object.

Slide: "SLIDE", and related "FOCUS", "FOV", "CELL"
   Focus: "FOCUS", and related "FOV", "CELL"
   Field of View: "FOV", and related "CELL"
   Cell: "CELL"

E. Cellular Descriptor Features

When computing cell features, the features are reflected in one or more of the following cellular or sub-cellular localities: the whole cell (CELL), the nucleus (NUCL), the cytoplasm (CYTO) or the cell membrane (MEMB).

Whole cell: "CELL"
   Nucleus: "NUCL"
   Cytoplasm: "CYTO"
   Membrane: "MEMB"

APPENDIX OF TABLES

TABLE 1

List of exemplary markers and their respective sub-cellular localization.

| Marker Name | Localization |
| --- | --- |
| E2F1 | Nucleus |
| MUC-1 (IF3.9) | Membrane |
| NDRG-1 (ZYMED CAP43) | Cytoplasm (Nucleus + Membrane) |
| $p21^{ras}$ | Cytoplasm |
| p53 | Nucleus |
| Phospho p27 | Cytoplasm (Nucleus) |
| PSMB9 (3A2.4) | Cytoplasm |
| SLPI (5G6.24) | Cytoplasm |
| src | Cytoplasm |

TABLE 2

Dispatcher settings resulting in the affectation of selected cells into category 1, 2 or 3.

| Marker Targeted Cell Compartment | Dispatch Step | If Feature | Value Is (Transmittance) | Cell(s) | Is |
| --- | --- | --- | --- | --- | --- |
| Nucleus | 1 | NUCL_DYE2_OD_MEAN | > 0.161151 (69%) | All | (2 or 3) otherwise 1 |
|  | 2 | NUCL_DYE2_OD_MEAN | > 0.29243 (51%) | 2 and 3 | 3 otherwise 2 |
| Cytoplasmic | 1 | CYTO_DYE2_OD_MEAN | > 0.173925 (67%) | All | (2 or 3) otherwise 1 |
|  | 2 | CYTO_DYE2_OD_MEAN | > 0.29243 (51%) | 2 and 3 | 3 otherwise 2 |
| Membrane | 1 | CYTO_DYE2_OD_MEAN | > 0.06048 (87%) | All | (2 or 3) otherwise 1 |
|  |  | MEMB_DYE2_OD_MEAN | > 0.200659 (63%) |  |  |
|  |  | MEMB_AREA | > 150 pix. |  |  |
|  | 2 | CYTO_DYE2_OD_MEAN | > 0.173925 (67%) | 2 and 3 | 3 otherwise 2 |
|  |  | MEMB_DYE2_OD_MEAN | > 0.29243 (51%) |  |  |
|  |  | MEMB_AREA | > 150 pix. |  |  |

TABLE 3

Percentage Summary Features.

| Percentage of cells from categories | Feature Name |
| --- | --- |
| 0 | CELL_PERCENT_0 |
| 1 | CELL_PERCENT_1 |
| 2 | CELL_PERCENT_2 |
| 3 | CELL_PERCENT_3 |
| 0 and 1 | CELL_PERCENT_01 |
| 2 and 3 | CELL_PERCENT_23 |
| 0, 1 and 2 | CELL_PERCENT_012 |
| 1, 2 and 3 | CELL_PERCENT_123 |

TABLE 4

Description and Outcomes of Patients from which Body Samples were Taken (Experimental Example)

| Stage | Good | Bad | All |
| --- | --- | --- | --- |
| T1N0 | 60 | 20 | 80 |
| T1N1 | 6 | 7 | 13 |
| T2N0 | 59 | 39 | 98 |
| T3N0 | 6 | 10 | 16 |
| Totals | 131 | 76 | 207 |

TABLE 5

Percentage summary features for
Experimental Example (showing threshold values
determined for sequence-based decision rule).

| Marker | Feature | Threshold | Rule (1 if) |
|---|---|---|---|
| SLPI | CELL_PERCENT_01 | 99.887874 | < |
| p21ras | CELL_PERCENT_0 | 35.642851 | < |
| E2F1 | CELL_PERCENT_2 | 2.463659 | > |
| src | CELL_PERCENT_1 | 37.624326 | > |

TABLE 6

Sensitivity and Specificity couples using
sequence interpretation approach for SLPI,
p21ras, E2F1 and SRC combination from
Experimental Example. (Sequence S0110 must be
read as follows: SLPI = OFF/p21ras = ON/
E2F1 = ON/src = OFF.)

SLPI-p21ras-E2F1-src

| Sequence | CumulBad | CumulGood | Sensitivity | Specificity |
|---|---|---|---|---|
| S1111 | 4 | 0 | 0.069 | 1 |
| S1011 | 7 | 0 | 0.1207 | 1 |
| S1110 | 12 | 0 | 0.2069 | 1 |
| S0111 | 14 | 8 | 0.2414 | 0.9184 |
| S1010 | 22 | 12 | 0.3793 | 0.8776 |
| S1101 | 26 | 14 | 0.4483 | 0.8571 |
| S0011 | 31 | 16 | 0.5345 | 0.8367 |
| S0110 | 35 | 19 | 0.6034 | 0.8061 |
| S1001 | 37 | 24 | 0.6379 | 0.7551 |
| S1100 | 37 | 26 | 0.6379 | 0.7347 |
| S0010 | 39 | 37 | 0.6724 | 0.6224 |
| S0101 | 41 | 40 | 0.7069 | 0.5918 |
| S1000 | 46 | 56 | 0.7931 | 0.4286 |
| S0001 | 49 | 63 | 0.8448 | 0.3571 |
| S0100 | 52 | 71 | 0.8966 | 0.2755 |
| S0000 | 58 | 98 | 1 | 0 |

TABLE 7

Details of $X^2$ analysis formulas resulting in the computation of
a $X^2$ value for the Good outcome patients ($X^2_{Good}$) and a $X^2$ value for Bad
Outcome patients ($X^2_{Bad}$).

| Good outcomes | | | |
|---|---|---|---|
| Sequence | Observed | Theoretical | Weighted Deviation |
| 00 | a | P(00|Good) × S | (a − P(00|Good) × S)$^2$/( P(00|Good) × S) |
| 01 | b | P(01|Good) × S | (b − P(01|Good) × S)$^2$/( P(01|Good) × S) |
| 10 | c | P(10|Good) × S | (c − P(10|Good) × S)$^2$/( P(10|Good) × S) |
| 11 | d | P(11|Good) × S | (d − P(11|Good) × S)$^2$/( P(11|Good) × S) |
| Sum | S = (a + b + c + d) | S | $X^2_{Good}$ |

H$_0$Good: Markers are independent regarding Good outcome patients

| Bad outcomes | | | |
|---|---|---|---|
| Sequence | Observed | Theoretical | Weighted Deviation |
| 00 | a | P(00|Bad) × S | (a − P(00|Bad) × S)$^2$/( P(00|Bad) × S) |
| 01 | b | P(01|Bad) × S | (b − P(01|Bad) × S)$^2$/( P(01|Bad) × S) |
| 10 | c | P(10|Bad) × S | (c − P(10|Bad) × S)$^2$/( P(10|Bad) × S) |
| 11 | d | P(11|Bad) × S | (d − P(11|Bad) × S)$^2$/( P(11|Bad) × S) |
| Sum | S = (a + b + c + d) | S | $X^2_{Bad}$ |

H$_0$Bad: Markers are independent regarding Bad outcome patients

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

That which is claimed:

1. A method for analyzing at least one marker to determine a prognosis of a cancer patient, said method comprising:
    exposing a body sample to: (i) the at least one marker indicated by a dye, and (ii) at least one other dye, the body sample taken from the cancer patient;
    extracting at least one quantifiable feature from an image taken of at least one slide using an image processing system, the at least one slide being prepared using the body sample exposed to the at least one marker, and the at least one quantifiable feature being determined at least in part by a chromogen separation of the image into relative amounts of each of the dyes in each pixel of the image;
    applying a decision rule to the at least one quantifiable feature, so as to determine the prognosis of the cancer patient based on a relationship between the at least one quantifiable feature and the decision rule.

2. A method according to claim 1, wherein the applying step further comprises applying a threshold to the at least one quantifiable feature so as to determine the prognosis of the cancer patient based on a relationship between the at least one quantifiable feature and the threshold.

3. A method according to claim 2, wherein the applying step further comprises applying an affectation rule for the threshold, the affectation rule being capable of establishing a either a good prognosis or a bad prognosis corresponding to a value of the at least one quantifiable feature in relation to the threshold.

4. A method according to claim 1, wherein the extracting step further comprises identifying a region of interest from which to extract the at least one quantifiable feature, the region of interest being within the image taken of the at least one slide using the image processing system.

5. A method according to claim 1, wherein the at least one marker is selected from the group consisting of:
colorimetric biomarkers;
SLPI;
PSMB9;
NDRG-1;
Muc-1;
phospho-p27;
Src;
E2F1;
p21 ras;
p53; and
combinations thereof.

6. A method according to claim 1, wherein the at least one quantifiable feature is selected from the group consisting of:
transmittance;
optical density;
cell morphology;
percentage of cell types characterized by marker intensity and cell morphology; and
combinations thereof.

7. A method according to claim 1, further comprising generating an image of the at least one slide using the image processing system, wherein the extracting step comprises extracting the at least one quantifiable feature from the generated image using the image processing system.

8. A method according to claim 1, further comprising communicating the at least one quantifiable feature from the image processing system to a controller, wherein the controller is configured to control the image processing system, and wherein the applying step is performed by the controller.

9. A method according to claim 1, wherein the at least one quantifiable feature is determined at least in part from a chromogen separation of the image into relative concentrations of each of the dyes in each pixel of the image.

10. A method according to claim 1, wherein the at least one quantifiable feature comprises a transmittance and an optical density of the dyes in each pixel of the image determined at least in part from a chromogen separation of the image.

11. A computer program product capable of controlling an image processing system to analyze at least one marker to determine a prognosis of a cancer patient, the computer program product comprising a computer-readable storage medium having computer-readable program code portions stored therein, the computer-readable program code portions comprising:
an executable portion for extracting at least one quantifiable feature from an image taken of at least one slide using an image processing system, the at least one slide being prepared using a body sample exposed to: (i) the at least one marker indicated by a dye, and (ii) at least one other dye, the body sample taken from the cancer patient, and the at least one quantifiable feature being determined at least in part by a chromogen separation of the image into relative amounts of each of the dyes in each pixel of the image; and
an executable portion for applying a decision rule to the at least one quantifiable feature, so as to determine the prognosis of the cancer patient based on a relationship between the at least one quantifiable feature and the decision rule.

12. A computer program product according to claim 11, wherein the executable portion for applying further comprises an executable portion for applying a threshold to the at least one quantifiable feature so as to determine the prognosis of the cancer patient based on a relationship between the at least one quantifiable feature and the threshold.

13. A computer program product according to claim 12, wherein the executable portion for applying further comprises an executable portion for applying an affectation rule for the threshold, the affectation rule being capable of establishing a either a good prognosis or a bad prognosis corresponding to a value of the at least one quantifiable feature in relation to the threshold.

14. A method for evaluating at least one marker adapted to determine a prognosis of a cancer patient, said method comprising:
exposing a plurality of body samples to: (i) the at least one marker indicated by a dye, and (ii) at least one other dye, the plurality of body samples being taken from a corresponding plurality of patients, each patient having a known clinical outcome;
extracting at least one quantifiable feature from an image taken of each of a plurality of slides using an image processing system, the plurality of slides being prepared using the plurality of body samples exposed to the at least one marker and each corresponding to a respective patient, and the at least one quantifiable feature being determined at least in part by a chromogen separation of the image into relative amounts of each of the dyes in each pixel of the image;
applying a plurality of candidate decision rules to the at least one quantifiable feature of each of the plurality of slides so as to provide a candidate prognosis for each of a plurality of combinations of the plurality of candidate decision rules and the at least one quantifiable feature; and
selecting an optimal decision rule corresponding to an optimal prognosis, the optimal decision rule being selected from the candidate decision rules, for the at least one quantifiable feature, the optimal decision rule providing that the optimal prognosis for each of the plurality of slides optimally corresponds to the known clinical outcome for each of the plurality of patients.

15. A method according to claim 14, wherein the applying step further comprises applying a plurality of candidate thresholds to the at least one quantifiable feature so as to generate a plurality of candidate prognoses corresponding to each of the plurality of candidate thresholds for each of the plurality of body samples and wherein the selecting step further comprises selecting an optimal threshold value from the plurality of candidate thresholds such that the optimal prognosis for each of the plurality of slides optimally corresponds to the known clinical outcome for each of the plurality of patients.

16. A method according to claim 15, wherein the applying step further comprises determining an affectation rule for each of the plurality of candidate thresholds, the affectation rule being capable of establishing a either a good prognosis or a bad prognosis corresponding to a value of the at least one quantifiable feature in relation to each of the plurality of candidate thresholds.

17. A method according to claim 14, wherein the selecting step further comprises:
determining a plurality of specificity and sensitivity couples corresponding to each of the plurality of candidate decision rules;
plotting the plurality of specificity and sensitivity couples on a receiver operating characteristic curve;
computing a plurality of Euclidian distances between each of the plurality of specificity and sensitivity couples and an optimal specificity and sensitivity couple; and selecting the optimal decision rule corresponding to a specificity and sensitivity couple having a minimum Euclidian distance to the optimal specificity and sensitivity couple.

18. A method according to claim 14, wherein the extracting step further comprises identifying a region of interest from which to extract the at least one quantifiable feature, the region of interest being within the image taken of each of a plurality of slides using the image processing system.

19. A method according to claim 14, further comprising evaluating the statistical independence of the at least one marker so as to ensure that the at least one marker is capable of providing a prognosis that is statistically independent of at least one other marker.

20. A method according to claim 19, wherein the evaluating step further comprises:
    comparing a frequency distribution of observed outcomes to a frequency distribution of theoretical prognoses computed assuming that the at least one marker is independent of an additional marker for a first plurality of body samples exposed to the at least one marker and to the at least one other marker, the first plurality of body samples corresponding to patients having a known good clinical outcome;
    comparing a frequency distribution of observed outcomes to a frequency distribution of theoretical prognoses computed assuming that the at least one marker is independent of the additional marker for a second plurality of body samples exposed to the at least one marker and to the at least one other marker, the second plurality of body samples corresponding to patients having a known bad clinical outcome;
    assessing the independence of the at least one marker with respect to the at least one other marker.

21. A method according to claim 20, wherein the assessing step further comprises assessing the independence of the at least one marker with respect to the at least one other marker using a chi square analysis.

22. A method according to claim 14, wherein the at least one marker is selected from the group consisting of:
    colorimetric biomarkers;
    SLPI;
    PSMB9;
    NDRG-1;
    Muc-1;
    phospho-p27;
    src;
    E2F1;
    p21ras;
    p53; and
    combinations thereof.

23. A method according to claim 14, wherein the at least one quantifiable feature is selected from the group consisting of:
    transmittance;
    optical density;
    cell morphology;
    percentage of cell types characterized by marker intensity and cell morphology; and
    combinations thereof.

24. A computer program product capable of controlling an image processing system to evaluate at least one marker adapted to determine a prognosis of a cancer patient, the computer program product comprising a computer-readable storage medium having computer-readable program code portions stored therein, the computer-readable program code portions comprising:
    an executable portion for extracting at least one quantifiable feature from an image taken of each of a plurality of slides using an image processing system, the plurality of slides being prepared using a plurality of body samples exposed to: (i) the at least one marker indicated by a dye, and (ii) at least one other dye, each body sample taken from a respective one of a plurality of patients, each patient having a known clinical outcome, and the at least one quantifiable feature being determined at least in part by a chromogen separation of the image into relative amounts of each of the dyes in each pixel of the image;
    an executable portion for applying an exhaustive plurality of candidate decision rules to the at least one quantifiable feature of each of the plurality of slides so as to provide a candidate prognosis for each of a plurality of combinations of the exhaustive plurality of candidate decision rules and the at least one quantifiable feature; and
    an executable portion for selecting an optimal decision rule corresponding to an optimal prognosis, the optimal decision rule being selected from the candidate decision rules, for the at least one quantifiable feature, the optimal decision rule providing that the optimal prognosis for each of the plurality of slides optimally corresponds to the known clinical outcome for each of the plurality of patients.

25. A computer program product according to claim 24, wherein the executable portion for applying further comprises an executable portion for applying a plurality of candidate thresholds to the at least one quantifiable feature so as to generate a plurality of candidate prognoses corresponding to each of the plurality of candidate thresholds for each of the plurality of body samples and wherein the executable portion for selecting further comprises an executable portion for selecting an optimal threshold value from the plurality of candidate thresholds such that the optimal prognosis for each of the plurality of slides optimally corresponds to the known clinical outcome for each of the plurality of patients.

26. A computer program product according to claim 25, wherein the executable portion for applying a plurality of candidate thresholds further comprises an executable portion for determining an affectation rule for each of the plurality of candidate thresholds, the affectation rule being capable of establishing a either a good prognosis or a bad prognosis corresponding to a value of the at least one quantifiable feature in relation to each of the plurality of candidate thresholds.

27. A computer program product according to claim 24, wherein the executable portion for selecting step further comprises:
    an executable portion for determining a plurality of specificity and sensitivity couples corresponding to each of the exhaustive plurality of candidate decision rules;
    an executable portion for plotting the plurality of specificity and sensitivity couples on a receiver operating characteristic curve;
    an executable portion for computing a plurality of Euclidian distances between each of the plurality of specificity and sensitivity couples and an optimal specificity and sensitivity couple; and
    an executable portion for selecting the optimal decision rule corresponding to a specificity and sensitivity couple having a minimum Euclidian distance to the optimal specificity and sensitivity couple.

28. A computer program product according to claim 24, wherein the executable portion for extracting further comprises an executable portion for identifying a region of interest from which to extract the at least one quantifiable feature, the region of interest being within the image taken of each of a plurality of slides using the image processing system.

29. A computer program product according to claim 24, further comprising an executable portion for evaluating the statistical independence of the at least one marker so as to ensure that the at least one marker is capable of providing a prognosis that is statistically independent of at least one other marker.

30. A computer program product according to claim 29, wherein the executable portion for evaluating further comprises:

an executable portion for comparing a frequency distribution of observed outcomes to a frequency distribution of theoretical prognoses for a first plurality of body samples exposed to the at least one marker and to the at least one other marker, the first plurality of body samples corresponding to patients having a known good clinical outcome;

an executable portion for comparing a frequency distribution of observed outcomes to a frequency distribution of theoretical prognoses for a second plurality of body samples exposed to the at least one marker and to the at least one other marker, the second plurality of body samples corresponding to patients having a known bad clinical outcome;

an executable portion for assessing the independence of the at least one marker with respect to the at least one other marker.

31. A computer program product according to claim 30, wherein the executable portion for assessing further comprises an executable portion for assessing the independence of the at least one marker with respect to the at least one other marker using a chi square analysis.

* * * * *